United States Patent
Dale et al.

(10) Patent No.: US 11,648,110 B2
(45) Date of Patent: May 16, 2023

(54) BRAIDED ANCHOR FOR MITRAL VALVE

(71) Applicant: Tendyne Holdings, Inc., St. Paul, MN (US)

(72) Inventors: Theodore Paul Dale, Corcoran, MN (US); David A. Panus, Maple Grove, MN (US); Paul Robinson, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 210 days.

(21) Appl. No.: 17/112,169

(22) Filed: Dec. 4, 2020

(65) Prior Publication Data

US 2021/0169645 A1 Jun. 10, 2021

Related U.S. Application Data

(60) Provisional application No. 62/943,882, filed on Dec. 5, 2019.

(51) Int. Cl.
*A61F 2/24* (2006.01)

(52) U.S. Cl.
CPC .......... *A61F 2/2418* (2013.01); *A61F 2/2427* (2013.01); *A61F 2220/0008* (2013.01)

(58) Field of Classification Search
CPC ........ A61F 2/24; A61F 2/2418; A61F 2/2457; A61F 2/2454; A61F 2/2478; A61F 2/2427; A61F 2/243; A61F 2/2433; A61F 2/2451
See application file for complete search history.

(56) References Cited

U.S. PATENT DOCUMENTS

| | | | |
|---|---|---|---|
| 2,697,008 A | 12/1954 | Ross | |
| 3,409,013 A | 11/1968 | Berry | |
| 3,472,230 A | 10/1969 | Fogarty et al. | |
| 3,476,101 A | 11/1969 | Ross | |
| 3,548,417 A | 12/1970 | Kischer | |
| 3,587,115 A | 6/1971 | Shiley | |
| 3,657,744 A | 4/1972 | Ersek | |
| 3,671,979 A | 6/1972 | Moulopoulos | |

(Continued)

FOREIGN PATENT DOCUMENTS

| | | |
|---|---|---|
| CN | 1486161 A | 3/2004 |
| CN | 1961845 A | 5/2007 |

(Continued)

OTHER PUBLICATIONS

US 9,155,620 B2, 10/2015, Gross et al. (withdrawn)

(Continued)

*Primary Examiner* — Seema Mathew
(74) *Attorney, Agent, or Firm* — Wei & Sleman LLP

(57) ABSTRACT

A prosthetic heart valve may include a valve portion, a tether connected to the valve portion, and an anchor for connecting the tether to the wall of the heart. The anchor may include a flexible first disc biased toward a first shape that is convex in a first direction and a neck extending from the first disc in a second direction opposite the first direction. The neck has a first end connected to the first disc and a second end. The anchor may further include a flexible second disc connected to the second end of the neck and biased toward a second shape that is convex in the first direction. When deployed, the first and second discs sandwich the wall of the heart.

15 Claims, 22 Drawing Sheets

(56) References Cited

U.S. PATENT DOCUMENTS

| | | | |
|---|---|---|---|
| 3,714,671 | A | 2/1973 | Edwards et al. |
| 3,755,823 | A | 9/1973 | Hancock |
| 3,976,079 | A | 8/1976 | Samuels et al. |
| 4,003,382 | A | 1/1977 | Dyke |
| 4,035,849 | A | 7/1977 | Angell et al. |
| 4,056,854 | A | 11/1977 | Boretos et al. |
| 4,073,438 | A | 2/1978 | Meyer |
| 4,106,129 | A | 8/1978 | Carpentier et al. |
| 4,222,126 | A | 9/1980 | Boretos et al. |
| 4,265,694 | A | 5/1981 | Boretos et al. |
| 4,297,749 | A | 11/1981 | Davis et al. |
| 4,339,831 | A | 7/1982 | Johnson |
| 4,343,048 | A | 8/1982 | Ross et al. |
| 4,345,340 | A | 8/1982 | Rosen |
| 4,373,216 | A | 2/1983 | Klawitter |
| 4,406,022 | A | 9/1983 | Roy |
| 4,470,157 | A | 9/1984 | Love |
| 4,490,859 | A | 1/1985 | Black et al. |
| 4,535,483 | A | 8/1985 | Klawitter et al. |
| 4,574,803 | A | 3/1986 | Storz |
| 4,585,705 | A | 4/1986 | Broderick et al. |
| 4,592,340 | A | 6/1986 | Boyles |
| 4,605,407 | A | 8/1986 | Black et al. |
| 4,612,011 | A | 9/1986 | Kautzky |
| 4,626,255 | A | 12/1986 | Reichart et al. |
| 4,638,886 | A | 1/1987 | Marietta |
| 4,643,732 | A | 2/1987 | Pietsch et al. |
| 4,655,771 | A | 4/1987 | Wallsten |
| 4,692,164 | A | 9/1987 | Dzemeshkevich et al. |
| 4,733,665 | A | 3/1988 | Palmaz |
| 4,759,758 | A | 7/1988 | Gabbay |
| 4,762,128 | A | 8/1988 | Rosenbluth |
| 4,777,951 | A | 10/1988 | Cribier et al. |
| 4,787,899 | A | 11/1988 | Lazarus |
| 4,787,901 | A | 11/1988 | Baykut |
| 4,796,629 | A | 1/1989 | Grayzel |
| 4,824,180 | A | 4/1989 | Levrai |
| 4,829,990 | A | 5/1989 | Thuroff et al. |
| 4,830,117 | A | 5/1989 | Capasso |
| 4,851,001 | A | 7/1989 | Taheri |
| 4,856,516 | A | 8/1989 | Hillstead |
| 4,878,495 | A | 11/1989 | Grayzel |
| 4,878,906 | A | 11/1989 | Lindemann et al. |
| 4,883,458 | A | 11/1989 | Shiber |
| 4,922,905 | A | 5/1990 | Strecker |
| 4,923,013 | A | 5/1990 | De Gennaro |
| 4,960,424 | A | 10/1990 | Grooters |
| 4,966,604 | A | 10/1990 | Reiss |
| 4,979,939 | A | 12/1990 | Shiber |
| 4,986,830 | A | 1/1991 | Owens et al. |
| 4,994,077 | A | 2/1991 | Dobben |
| 4,996,873 | A | 3/1991 | Takeuchi |
| 5,007,896 | A | 4/1991 | Shiber |
| 5,026,366 | A | 6/1991 | Leckrone |
| 5,032,128 | A | 7/1991 | Alonso |
| 5,035,706 | A | 7/1991 | Giantureo et al. |
| 5,037,434 | A | 8/1991 | Lane |
| 5,047,041 | A | 9/1991 | Samuels |
| 5,059,177 | A | 10/1991 | Towne et al. |
| 5,064,435 | A | 11/1991 | Porter |
| 5,080,668 | A | 1/1992 | Bolz et al. |
| 5,085,635 | A | 2/1992 | Cragg |
| 5,089,015 | A | 2/1992 | Ross |
| 5,152,771 | A | 10/1992 | Sabbaghian et al. |
| 5,163,953 | A | 11/1992 | Vince |
| 5,167,628 | A | 12/1992 | Boyles |
| 5,192,297 | A | 3/1993 | Hull |
| 5,201,880 | A | 4/1993 | Wright et al. |
| 5,266,073 | A | 11/1993 | Wall |
| 5,282,847 | A | 2/1994 | Trescony et al. |
| 5,295,958 | A | 3/1994 | Shturman |
| 5,306,296 | A | 4/1994 | Wright et al. |
| 5,332,402 | A | 7/1994 | Teitelbaum |
| 5,336,616 | A | 8/1994 | Livesey et al. |
| 5,344,442 | A | 9/1994 | Deac |
| 5,360,444 | A | 11/1994 | Kusuhara |
| 5,364,407 | A | 11/1994 | Poll |
| 5,370,685 | A | 12/1994 | Stevens |
| 5,397,351 | A | 3/1995 | Pavcnik et al. |
| 5,411,055 | A | 5/1995 | Kane |
| 5,411,552 | A | 5/1995 | Andersen et al. |
| 5,415,667 | A | 5/1995 | Frater |
| 5,443,446 | A | 8/1995 | Shturman |
| 5,480,424 | A | 1/1996 | Cox |
| 5,500,014 | A | 3/1996 | Quijano et al. |
| 5,545,209 | A | 8/1996 | Roberts et al. |
| 5,545,214 | A | 8/1996 | Stevens |
| 5,549,665 | A | 8/1996 | Vesely et al. |
| 5,554,184 | A | 9/1996 | Machiraju |
| 5,554,185 | A | 9/1996 | Block et al. |
| 5,571,175 | A | 11/1996 | Vanney et al. |
| 5,591,185 | A | 1/1997 | Kilmer et al. |
| 5,607,462 | A | 3/1997 | Imran |
| 5,607,464 | A | 3/1997 | Trescony et al. |
| 5,609,626 | A | 3/1997 | Quijano et al. |
| 5,639,274 | A | 6/1997 | Fischell et al. |
| 5,662,704 | A | 9/1997 | Gross |
| 5,665,115 | A | 9/1997 | Cragg |
| 5,674,279 | A | 10/1997 | Wright et al. |
| 5,697,905 | A | 12/1997 | d'Ambrosio |
| 5,702,368 | A | 12/1997 | Stevens et al. |
| 5,716,417 | A | 2/1998 | Girard et al. |
| 5,728,068 | A | 3/1998 | Leone et al. |
| 5,728,151 | A | 3/1998 | Garrison et al. |
| 5,735,842 | A | 4/1998 | Krueger et al. |
| 5,741,333 | A | 4/1998 | Frid |
| 5,749,890 | A | 5/1998 | Shaknovich |
| 5,756,476 | A | 5/1998 | Epstein et al. |
| 5,769,812 | A | 6/1998 | Stevens et al. |
| 5,792,179 | A | 8/1998 | Sideris |
| 5,800,508 | A | 9/1998 | Goicoechea et al. |
| 5,833,673 | A | 11/1998 | Ockuly et al. |
| 5,840,081 | A | 11/1998 | Andersen et al. |
| 5,855,597 | A | 1/1999 | Jayaraman |
| 5,855,601 | A | 1/1999 | Bessler et al. |
| 5,855,602 | A | 1/1999 | Angell |
| 5,904,697 | A | 5/1999 | Gifford, III et al. |
| 5,925,063 | A | 7/1999 | Khosravi |
| 5,957,949 | A | 9/1999 | Leonhardt et al. |
| 5,968,052 | A | 10/1999 | Sullivan, III et al. |
| 5,968,068 | A | 10/1999 | Dehdashtian et al. |
| 5,972,030 | A | 10/1999 | Garrison et al. |
| 5,993,481 | A | 11/1999 | Marcade et al. |
| 6,027,525 | A | 2/2000 | Suh et al. |
| 6,042,607 | A | 3/2000 | Williamson, IV et al. |
| 6,045,497 | A | 4/2000 | Schweich, Jr. et al. |
| 6,063,112 | A | 5/2000 | Sgro |
| 6,077,214 | A | 6/2000 | Mortier et al. |
| 6,099,508 | A | 8/2000 | Bousquet |
| 6,132,473 | A | 10/2000 | Williams et al. |
| 6,168,614 | B1 | 1/2001 | Andersen et al. |
| 6,171,335 | B1 | 1/2001 | Wheatley et al. |
| 6,174,327 | B1 | 1/2001 | Mertens et al. |
| 6,183,411 | B1 | 2/2001 | Mortier et al. |
| 6,210,408 | B1 | 4/2001 | Chandrasekaran et al. |
| 6,217,585 | B1 | 4/2001 | Houser et al. |
| 6,221,091 | B1 | 4/2001 | Khosravi |
| 6,231,602 | B1 | 5/2001 | Carpentier et al. |
| 6,245,102 | B1 | 6/2001 | Jayaraman |
| 6,260,552 | B1 | 7/2001 | Mortier et al. |
| 6,261,222 | B1 | 7/2001 | Schweich, Jr. et al. |
| 6,264,602 | B1 | 7/2001 | Mortier et al. |
| 6,287,339 | B1 | 9/2001 | Vazquez et al. |
| 6,299,637 | B1 | 10/2001 | Shaolian et al. |
| 6,302,906 | B1 | 10/2001 | Goicoechea et al. |
| 6,312,465 | B1 | 11/2001 | Griffin et al. |
| 6,332,893 | B1 | 12/2001 | Mortier et al. |
| 6,350,277 | B1 | 2/2002 | Kocur |
| 6,358,277 | B1 | 3/2002 | Duran |
| 6,379,372 | B1 | 4/2002 | Dehdashtian et al. |
| 6,402,679 | B1 | 6/2002 | Mortier et al. |
| 6,402,680 | B2 | 6/2002 | Mortier et al. |
| 6,402,781 | B1 | 6/2002 | Langberg et al. |
| 6,406,420 | B1 | 6/2002 | McCarthy et al. |

(56) References Cited

U.S. PATENT DOCUMENTS

| | | |
|---|---|---|
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |

(56) References Cited

U.S. PATENT DOCUMENTS

| | | |
|---|---|---|
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,579,963 B2 | 11/2013 | Tabor |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,364,325 B2 | 6/2016 | Alon et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,848,880 B2 * | 12/2017 | Coleman .......... A61B 17/12109 |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0055606 A1 | 3/2004 | Hendricksen et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Altieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0096735 A1 | 5/2005 | Hojeibane et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288763 A1 | 12/2005 | Andreas et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |

(56) References Cited

U.S. PATENT DOCUMENTS

| | | |
|---|---|---|
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2006/0287719 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0088431 A1 | 4/2007 | Bourang et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0054976 A1 | 2/2009 | Tuval et al. |
| 2009/0062841 A1* | 3/2009 | Amplatz .......... A61B 17/12159 606/200 |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0234940 A1 | 9/2010 | Dolan |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |

(56) References Cited

U.S. PATENT DOCUMENTS

| | | |
|---|---|---|
| 2011/0015729 A1 | 1/2011 | Jimenez et al. |
| 2011/0029072 A1 | 2/2011 | Gabbay |
| 2011/0046712 A1 | 2/2011 | Melsheimer et al. |
| 2011/0054519 A1* | 3/2011 | Neuss ............ A61B 17/12177 606/213 |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0301703 A1 | 12/2011 | Glazier |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0078347 A1 | 3/2012 | Braido et al. |
| 2012/0083874 A1 | 4/2012 | Dale et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0239142 A1 | 9/2012 | Liu et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0059747 A1 | 3/2013 | Mann et al. |
| 2013/0066341 A1 | 3/2013 | Ketai et al. |
| 2013/0079873 A1 | 3/2013 | Migliazza et al. |
| 2013/0110228 A1 | 5/2013 | Braido |
| 2013/0131788 A1 | 5/2013 | Quadri et al. |
| 2013/0172978 A1* | 7/2013 | Vidlund ............ A61B 17/0401 623/1.12 |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0268064 A1 | 10/2013 | Duffy |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1* | 12/2013 | Khalil ................ A61F 2/2427 623/2.11 |
| 2013/0338752 A1 | 12/2013 | Geusen et al. |
| 2014/0005767 A1 | 1/2014 | Glazier et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0128963 A1 | 5/2014 | Quill et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0316518 A1 | 10/2014 | Kheradvar et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305867 A1 | 10/2015 | Liu et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1* | 11/2016 | Vidlund ................ A61F 2/2436 |

(56) References Cited

U.S. PATENT DOCUMENTS

| | | | |
|---|---|---|---|
| 2016/0331527 A1 | 11/2016 | Vidlund et al. | |
| 2016/0346086 A1 | 12/2016 | Solem | |
| 2016/0367365 A1 | 12/2016 | Conklin | |
| 2016/0367367 A1 | 12/2016 | Maisano et al. | |
| 2016/0367368 A1 | 12/2016 | Vidlund et al. | |
| 2017/0079790 A1* | 3/2017 | Vidlund | A61B 17/0401 |
| 2017/0100248 A1 | 4/2017 | Tegels et al. | |
| 2017/0128208 A1 | 5/2017 | Christianson et al. | |
| 2017/0181854 A1 | 6/2017 | Christianson et al. | |
| 2017/0196688 A1 | 7/2017 | Christianson et al. | |
| 2017/0216028 A1* | 8/2017 | Khalil | A61B 17/064 |
| 2017/0252153 A1 | 9/2017 | Chau et al. | |
| 2017/0258589 A1 | 9/2017 | Pham et al. | |
| 2017/0266001 A1 | 9/2017 | Vidlund et al. | |
| 2017/0281343 A1* | 10/2017 | Christianson | A61F 2/2439 |
| 2017/0312076 A1 | 11/2017 | Lutter et al. | |
| 2017/0312077 A1* | 11/2017 | Vidlund | A61F 2/2439 |
| 2017/0312078 A1* | 11/2017 | Krivoruchko | A61F 2/2457 |
| 2017/0319333 A1* | 11/2017 | Tegels | A61B 17/0401 |
| 2018/0028314 A1 | 2/2018 | Ekvall et al. | |
| 2018/0078368 A1 | 3/2018 | Vidlund et al. | |
| 2018/0078370 A1* | 3/2018 | Kovalsky | A61F 2/2433 |
| 2018/0147055 A1 | 5/2018 | Vidlund et al. | |
| 2018/0193138 A1 | 7/2018 | Vidlund | |
| 2018/0263618 A1 | 9/2018 | Vidlund et al. | |
| 2018/0318071 A1* | 11/2018 | Lozonschi | A61F 2/2412 |
| 2018/0318083 A1* | 11/2018 | Bolling | A61M 25/0054 |
| 2019/0110796 A1* | 4/2019 | Jayaraman | A61B 17/12168 |
| 2019/0183642 A1* | 6/2019 | Tegels | A61F 2/2439 |
| 2020/0022810 A1 | 1/2020 | Christianson et al. | |
| 2020/0282204 A1* | 9/2020 | Capek | A61N 1/3629 |
| 2021/0000596 A1* | 1/2021 | Rajagopal | A61F 2/2418 |
| 2021/0030537 A1* | 2/2021 | Tegels | A61F 2/2409 |
| 2021/0186687 A1* | 6/2021 | Danielson | A61F 2/2457 |
| 2021/0236287 A1* | 8/2021 | Huddleston | A61F 2/2412 |
| 2021/0369257 A1* | 12/2021 | Huddleston | A61B 17/3478 |
| 2022/0000616 A1* | 1/2022 | Rajagopal | A61F 2/2457 |
| 2022/0015899 A1* | 1/2022 | Huddleston | A61F 2/2418 |
| 2022/0054256 A1* | 2/2022 | Huddleston | A61F 2/24 |
| 2022/0054259 A1* | 2/2022 | Osterbauer | A61F 2/2418 |
| 2023/0025890 A1* | 1/2023 | Marnach | A61F 2/2418 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 2246526 | 3/1973 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2007509700 A | 4/2007 |
| JP | 2008504078 A | 2/2008 |
| JP | 2008541863 A | 11/2008 |
| JP | 2009511229 A | 3/2009 |
| JP | 2009514628 A | 4/2009 |
| JP | 2009519783 A | 5/2009 |
| JP | 2012504031 A | 2/2012 |
| JP | 2012518465 A | 8/2012 |
| JP | 2012519024 A | 8/2012 |
| JP | 2013512765 A | 4/2013 |
| JP | 2013525039 A | 6/2013 |
| JP | 2013538086 A | 10/2013 |
| JP | 2014513585 A | 6/2014 |
| NL | 1017275 C2 | 8/2002 |
| SU | 1271508 | 11/1986 |
| SU | 1271508 A1 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200047139 A1 | 8/2000 |
| WO | 2001035878 A2 | 5/2001 |
| WO | 0149213 A2 | 7/2001 |
| WO | 200149213 A3 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 200176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 0236048 A1 | 5/2002 |
| WO | 2002036048 A1 | 5/2002 |
| WO | 2002041789 A2 | 5/2002 |
| WO | 2002043620 A1 | 6/2002 |
| WO | 2002049540 A2 | 6/2002 |
| WO | 02076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006005082 A2 | 1/2006 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009094500 A1 | 7/2009 |
| WO | 2009132187 A1 | 10/2009 |
| WO | 2010022138 A2 | 2/2010 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |

(56) References Cited

FOREIGN PATENT DOCUMENTS

| | | |
|---|---|---|
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013028387 A2 | 2/2013 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014071077 A1 | 5/2014 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |
| WO | 2019144121 A1 | 7/2019 |
| WO | WO-2019144121 A1 * 7/2019 ........... A61F 2/2418 |

OTHER PUBLICATIONS

"Shape Memory Alloys," Retrieved from the Internet: <http://webdocs.cs.ualberta.ca/~database/MEMS/sma.html>, Feb. 5, 2016, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Domplications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2): 102-106.
Australian Examination Report for Application No. 2016248314 dated Oct. 4, 2019, pp. 1-5.
Australian Examination Report for Application No. 2016248314 dated Sep. 30, 2019, pp. 1-5.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Examination Report for European Application No. 14734333.9, dated Oct. 20, 2016, 6 pages.
Examination Report No. 1 for Australian Application No. 2014274056, dated Mar. 6, 2018, 4 pages.
Examination Report No. 2 for Australian Application No. 2014274056, dated May 9, 2018, 2 pages.
Extended European Search Report for European Application No. 18160595.7, dated Sep. 14, 2018, 7 pages.
Extended European Search Report including Written Opinion for Application No. EP20168419.8, dated Jul. 21, 2020, pp. 1-8.
Extended European Search Report issued in Appln. No. 21165656.6 dated Aug. 11, 2021 (2 pages).
G. M. Bernacca, et al., "Polyurethane Heart Valves: Fatigue Failure, Calcification, and Polyurethane Structure," Journa of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2014/040188, dated Nov. 17, 2014, 12 pages.
Invitation to Pay Additional Fees and Partial International Search Report for International Application No. PCT/US2014/040188, dated Sep. 8, 2014, 5 pages.
Japanese Office Action for Application No. 2020105100, dated Jun. 4, 2021, 4 pages.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.
L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.
Lawrence, D. D., "Percutaneous Endovascular Graft: Experimental Evaluation," Radiology, 1987, 163:357-360.

(56) References Cited

OTHER PUBLICATIONS

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic Valve," ASAIO Journal, Sep./ Oct. 1996, 42(5):M381-M385.
Notice of Reasons for Rejection for Japanese Application No. 2016-517032, dated Feb. 13, 2018, 5 pages.
Office Action for Chinese Application No. 201480037269.5, dated Dec. 23, 2016.
Office Action for U.S. Appl. No. 14/950,656, dated Apr. 22, 2016, 5 pages.
Orton, C., "Mitralseal: Hybrid Transcatheter Mitral Valve Replacement," Symposium: Small Animal Proceedings, 2011, pp. 311-312.
Pavcnik, D. et al. "Development and Initial Experimental Evaluation of a Prosthetic Aortic Valve for Transcatheter Placement," Radiology, 1992; 183:151-154.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Rosch, J. et al., "The Birth, Early Years and Future of Interventional Radiology," J Vasc Interv Radiol, Jul. 2003, 4:841-853.
Ross, D. N., "Aortic Valve Surgery," Guys Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Search Report for CN201680033815.7 dated Nov. 1, 2019, 3 pages.
Second Office Action for Chinese Application No. 201480037269.5, dated Nov. 6, 2017, 6 pages.
Selby, M.D., J. Bayne, "Experience with New Retrieval Forceps for Foreign Body Removal in the Vascular, Urinary, and Biliary Systems," Radiology 1990; 176:535-538.
Serruys, p. W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Third Office Action for Chinese Application No. 201480037269.5, dated Jun. 19, 2018, 8 pages.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
U.S. Pat. No. 9,155,620, filed Oct. 2015, Gross et al. (withdrawn).
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
Dale, Theodore, et al., U.S. Appl. No. 17/112,169, filed Dec. 4, 2020, Titled "Braided Anchor For Mitral Valve".
Extended European Search Report including Written Opinion for EP20211930.1 dated Apr. 28, 2021; 8 pages.

\* cited by examiner

BRAIDED ANCHOR FOR MITRAL VALVE

CROSS REFERENCE TO RELATED APPLICATIONS

The present application claims the benefit of the filing date of U.S. Provisional Patent Application No. 62/943,882 filed Dec. 5, 2019, the disclosure of which is hereby incorporated herein by reference.

BACKGROUND

Valvular heart disease, and specifically aortic and mitral valve disease, is a significant health issue in the United States. Annually, approximately 90,000 valve replacements are performed in the United States. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated with the procedure, largely due to the necessity for extra-corporeal circulation. Further, open heart surgery is often poorly tolerated in elderly patients. Thus, if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated with the native mitral valve and thus a greater level of difficulty with regard to inserting and anchoring the replacement prosthesis.

Recent developments in the field have provided devices and methods for mitral valve replacement with reduced invasion and risk to the patient. Such devices typically include a prosthetic valve disposed within the native valve annulus and held in place with an anchor seated against an exterior surface of the heart near the apex, and such anchors must be at least a certain size to seat against the heart with adequate security. Methods of implanting such devices therefore typically require providing an intercostal puncture of significant size to accommodate the anchor. Trauma to the patient increases as a function of the diameter of the puncture. Accordingly, methods and devices for anchoring a prosthetic heart valve that reduce the diameter of any intercostal puncture, or avoid the need for a intercostal puncture altogether, would improve patient outcomes.

BRIEF SUMMARY

In some arrangements, an anchor for a prosthetic heart valve may include a flexible first disc biased toward a first dome shape that is convex in a first direction and a neck extending from the first disc in a second direction opposite the first direction. The neck may have a first end connected to the first disc and a second end. The anchor may further include a flexible second disc connected to the second end of the neck and biased toward a second dome shape that is convex in the first direction.

In further arrangements, a prosthetic heart valve may include a valve portion including at least two leaflets, a tether having a first end connected to the valve portion and a second end, and a flexible anchor connected to the second end of the tether. The anchor may include a flexible first disc biased toward a shape that is convex in a first direction, a flexible second disc connected to the first disc and biased toward a shape that is convex in the first direction, and a cuff securing the second disc to the tether.

In further arrangements, a prosthetic heart valve may include a valve portion having at least two leaflets, a tether having a first end connected to the valve portion and a second end, and a flexible anchor connected to the second end of the tether. The anchor may include a flexible first disc biased toward a first dome shape that is convex in a first direction, a neck having a first end connected to the first disc and extending in a second direction opposite the first direction to a second end, and a flexible second disc connected to the second end of the neck. The second disc may be biased toward a second dome shape that is convex in the first direction. The first disc, the neck, and the second disc may be formed from a contiguous tube of wire mesh. An elastically deformable frame may support the first disc. The frame may be invertible and biased toward a cone shape. An annular cuff may secure the second disc to the tether.

DETAILED DESCRIPTION

As used herein, the term "proximal," when used in connection with a delivery device or components of a delivery device, refers to the end of the device closer to the user of the device when the device is being used as intended. On the other hand, the term "distal," when used in connection with a delivery device or components of a delivery device, refers to the end of the device farther away from the user when the device is being used as intended. As used herein, the terms "substantially," "generally," "approximately," and "about" are intended to mean that slight deviations from absolute are included within the scope of the term so modified.

Figure 1:
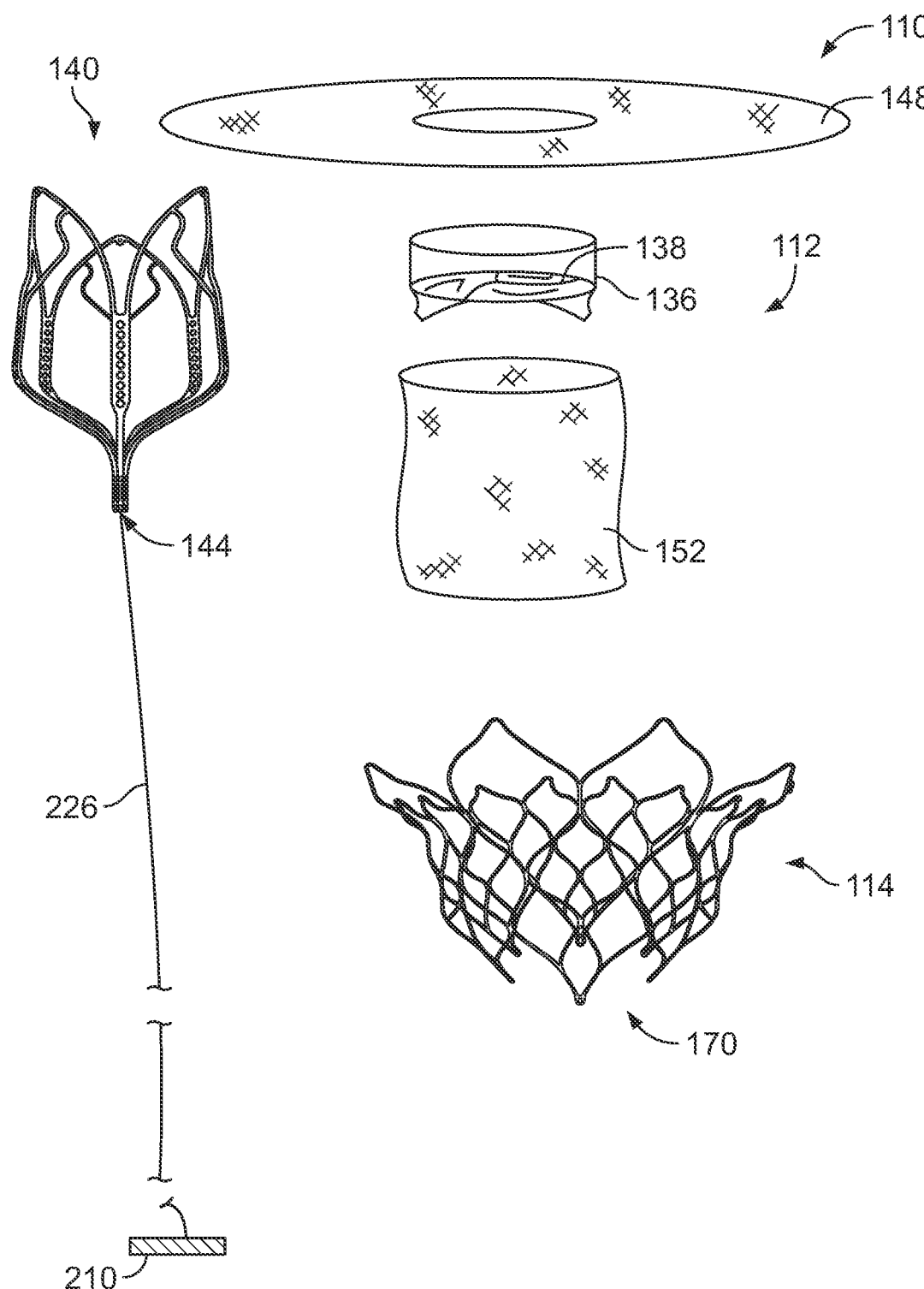
FIG. 1 is an exploded view of an exemplary prosthetic cardiovascular valve.

An exemplary prosthetic heart valve 110 as may be used with various embodiments of the present disclosure is shown in an exploded view in FIG. 1. Valve 110 includes an inner structure or assembly 112 and an outer structure or assembly 114. Valve 110 may be coupled to a tether 226 and a collapsible tether anchor 210.

Inner assembly 112 includes an inner frame 140, outer cylindrical wrap 152, and leaflet structure 136 (including articulating leaflets 138 that define a valve function). Leaflet structure 136 may be sewn to inner frame 140, and may use parts of inner frame 140 for this purpose. Inner assembly 112 is disposed and secured within outer assembly 114, as described in more detail below.

Outer assembly 114 includes outer frame 170. Outer frame 170 may also have in various embodiments an outer frame cover of tissue or fabric (not pictured), or may be left without an outer cover to provide exposed wireframe to facilitate in-growth of tissue. Outer frame 170 may also have an articulating collar or cuff (not pictured) covered by a cover 148 of tissue or fabric.

Tether 226 is connected to valve 110 by inner frame 140. Thus, inner frame 140 includes tether connecting or clamping portion 144 by which inner frame 140, and by extension valve 110, is coupled to tether 226.

Figure 2:
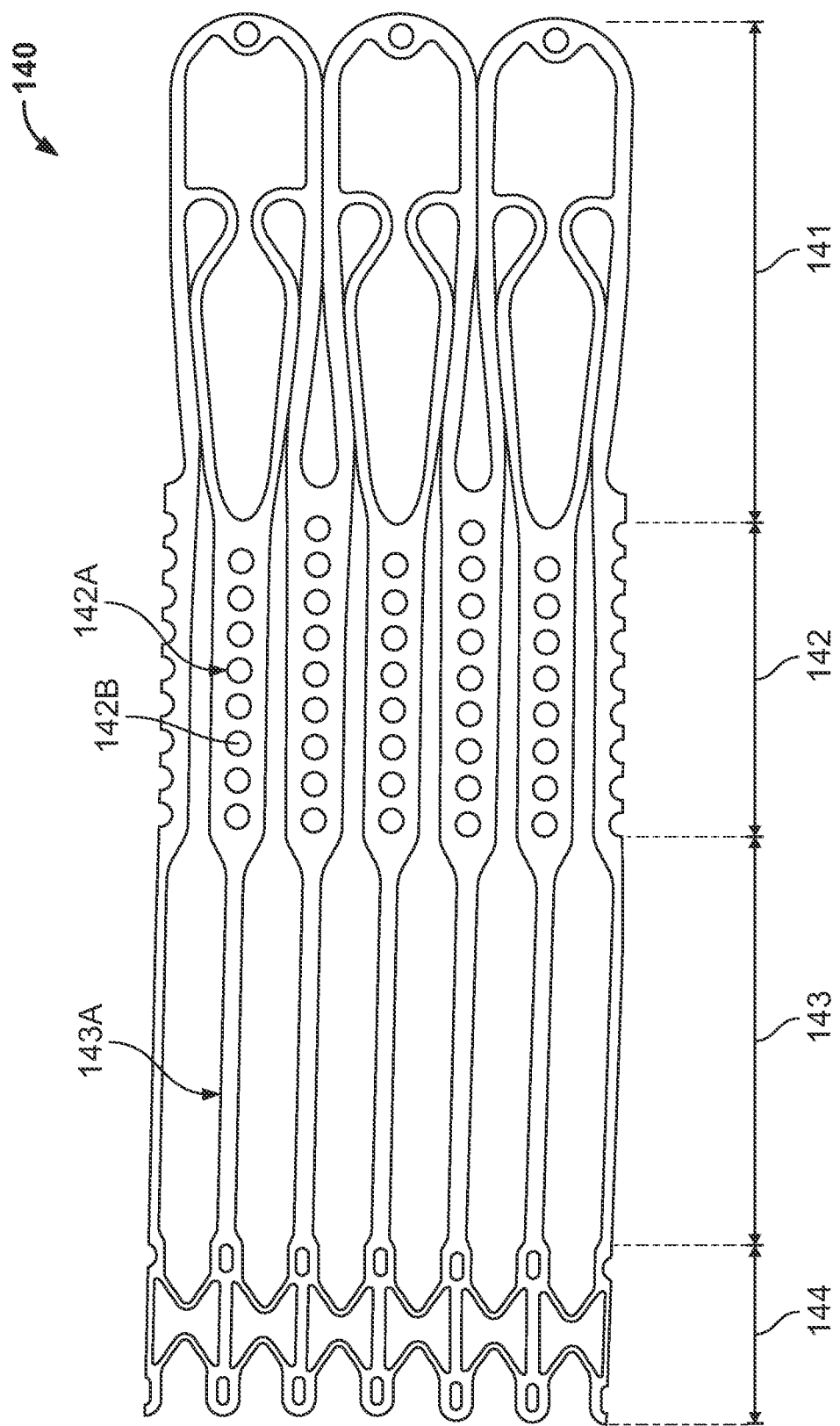
FIG. 2 is an opened and flattened view of an unexpanded inner frame of the prosthetic valve of FIG. 1.
Figure 3:
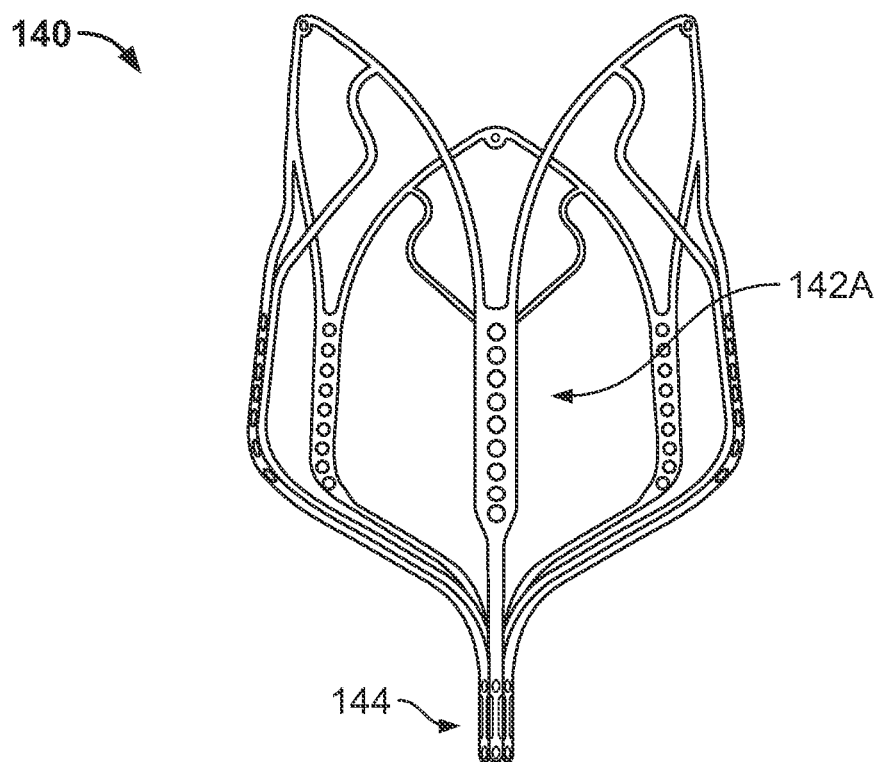
FIGS. 3 and 4 are side and bottom views, respectively, of the inner frame of FIG. 2 in an expanded configuration.
Figure 4:
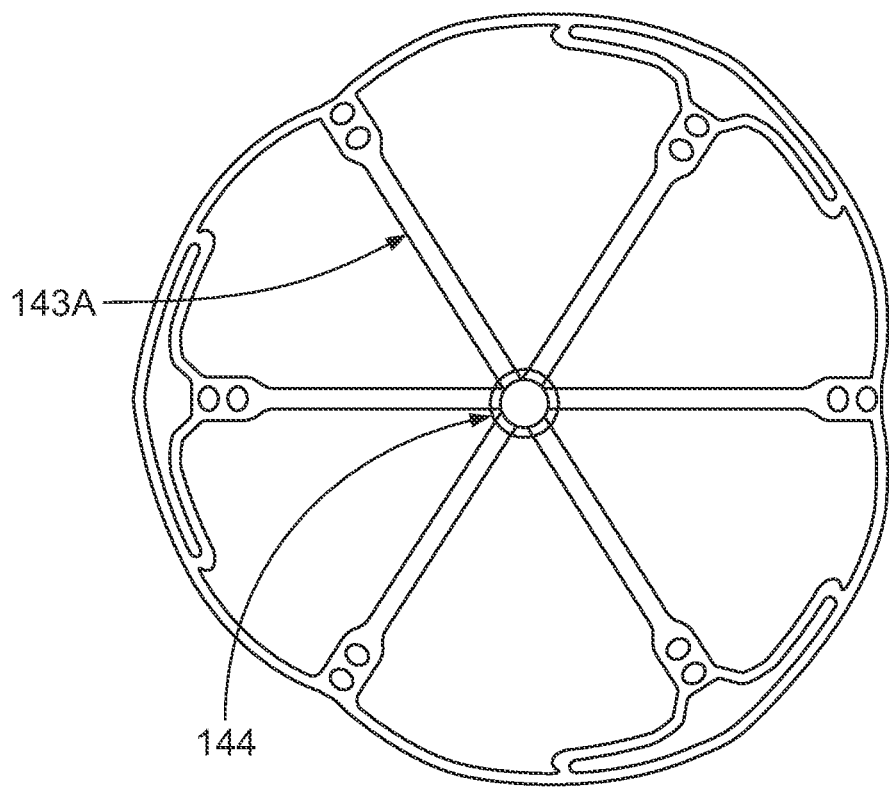

Inner frame 140 is shown in more detail in FIGS. 2-4. Inner frame 140 can be formed from a milled or laser-cut tube of a shape-memory material such as, for example, nitinol. Inner frame 140 is illustrated in FIG. 2 in an undeformed, initial state, i.e., as milled or laser-cut, but cut longitudinally and unrolled into a flat sheet for ease of illustration. Inner frame 140 is shown fully deformed, i.e., to the final, deployed configuration, in the side view and bottom view of FIGS. 3 and 4, respectively. Inner frame 140 can be divided into four portions corresponding to functionally different portions of inner frame 140 in final form: apex portion 141, body portion 142, strut portion 143, and tether connecting portion 144. Strut portion 143 includes six struts, such as strut 143A, which connect body portion 142 to connecting portion 144. A greater or lesser number of struts is contemplated herein.

Connecting portion 144 includes longitudinal extensions of the struts, connected circumferentially to one another by pairs of micro-V's. Connecting portion 144 is configured to be radially collapsed by application of a compressive force, which causes the micro-V's to become more deeply V-shaped, with each pair of vertices moving closer together longitudinally and the open ends of the V shapes moving closer together circumferentially. When collapsed, connecting portion 144 can clamp or grip one end of tether 226, either connecting directly onto a tether line (e.g., braided filament line) or onto an intermediate structure, such as a polymer or metal piece that is, in turn, firmly fixed to the tether line. The foregoing is merely exemplary and other techniques can be used to connect tether 226 to connecting portion 144.

In contrast to connecting portion 144, apex portion 141 and body portion 142 are configured to be expanded radially. Strut portion 143 forms a longitudinal connection, and radial transition, between the expanded body portion 142 and the compressed connecting portion 144.

Body portion 142 includes six longitudinal posts, such as post 142A, although the body portion may include a greater or lesser number of such posts. The posts can be used to attach leaflet structure 136 to inner frame 140, and/or can be used to attach inner assembly 112 to outer assembly 114, such as by connecting inner frame 140 to outer frame 170. In the illustrated example, posts 142A include apertures 142B through which connecting members (such as suture filaments and/or wires) can be passed to couple the posts to other structures.

Figure 5:
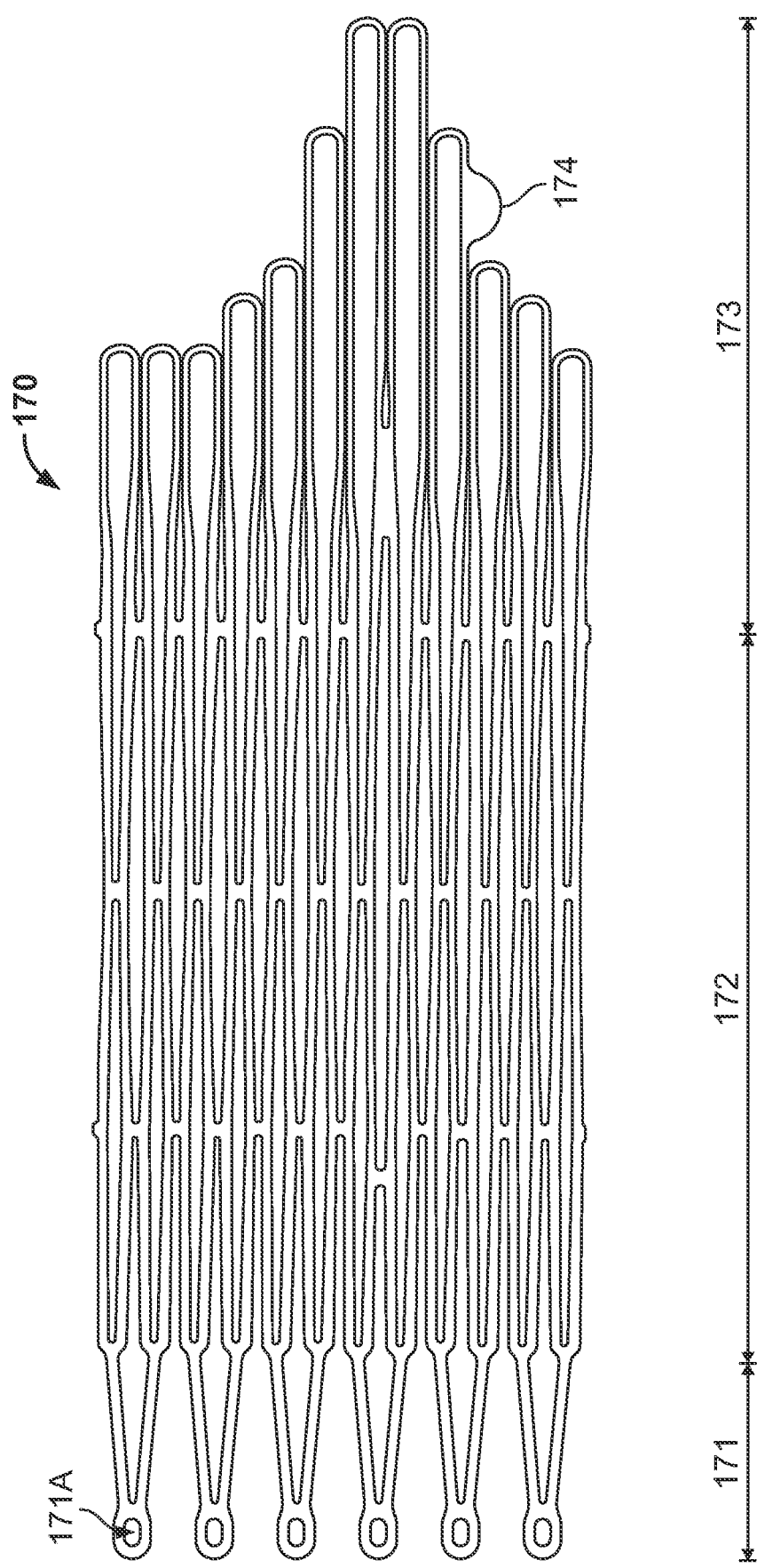
FIG. 5 is an opened and flattened view of an unexpanded outer frame of the prosthetic valve of FIG. 1.
Figure 6:
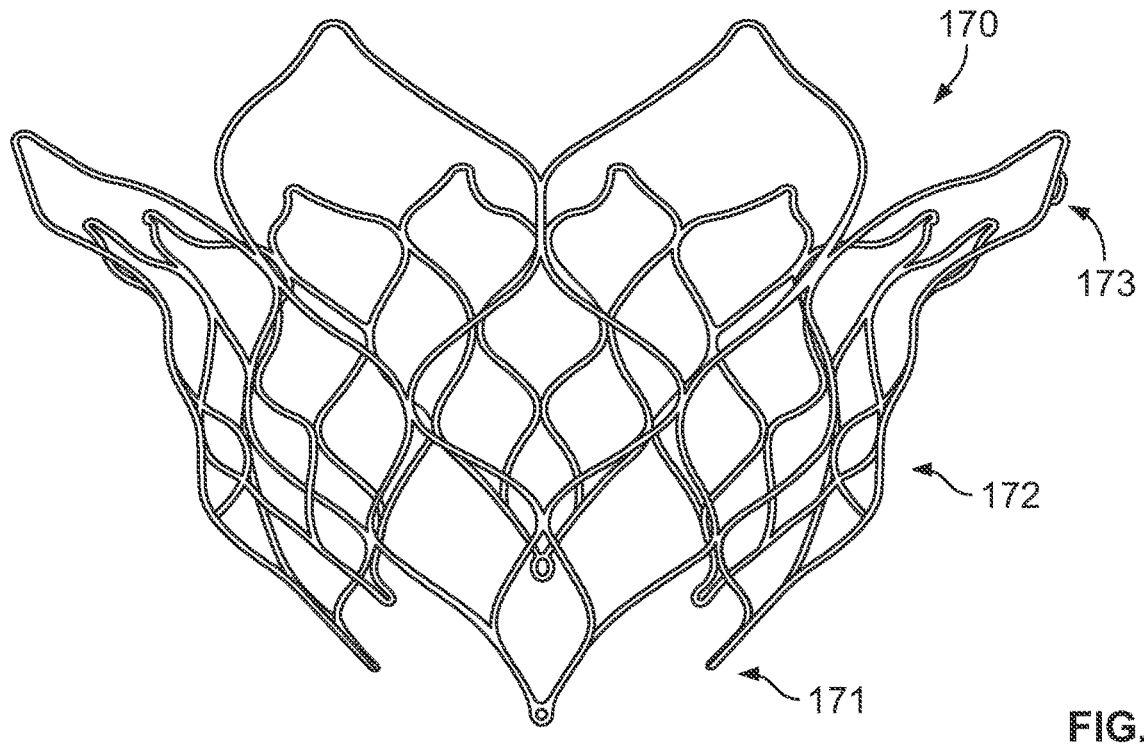
FIGS. 6 and 7 are side and top views, respectively, of the outer frame of FIG. 5 in an expanded configuration.
Figure 7:
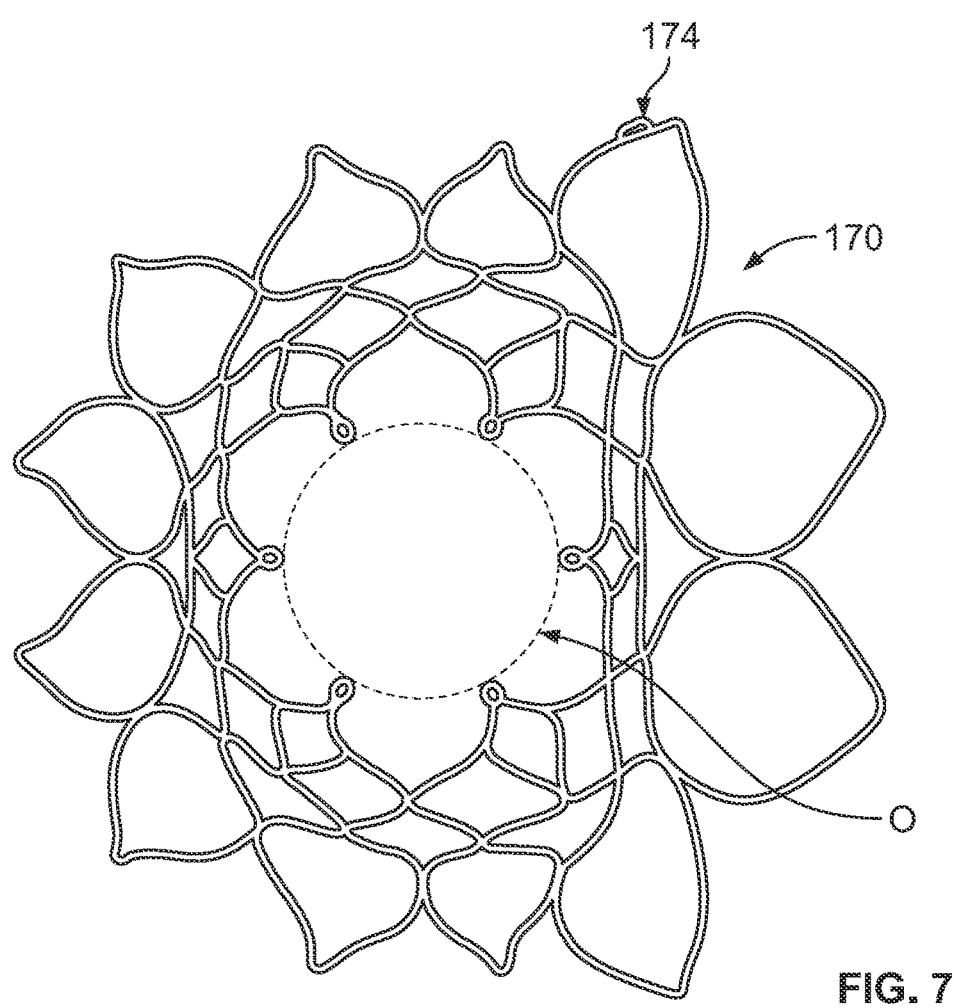

Outer frame 170 of valve 110 is shown in more detail in FIGS. 5-7. Outer frame 170 can be formed from a milled or laser-cut tube of a shape-memory material such as, for example, nitinol. Outer frame 170 is illustrated in FIG. 5 in an undeformed, initial state, i.e., as milled or laser-cut, but cut longitudinally and unrolled into a flat sheet for ease of illustration. Outer frame 170 can be divided into a coupling portion 171, a body portion 172, and a flared portion 173, as shown in FIG. 5. Coupling portion 171 includes multiple openings or apertures 171A by which outer frame 170 can be coupled to inner frame 140, as discussed in more detail below.

Flared portion 173 may include an indicator 174. In one example, indicator 174 is simply a broader portion of the wire frame element of flared portion 173, i.e., indicator 174 is more apparent in radiographic or other imaging modalities than the surrounding wireframe elements of flared portion 173. In other examples, indicator 174 can be any distinguishable feature (e.g., protrusion, notch, etc.) and/or indicia (e.g., lines, markings, tic marks, etc.) that enhance the visibility of the part of flared portion 173 on which it is formed, or to which it is attached. Indicator 174 can facilitate the implantation of the prosthetic valve by providing a reference point or landmark that the operator can use to orient and/or position the valve (or any portion of the valve) with respect to the native valve annulus or other heart structure. For example, during implantation, an operator can identify (e.g., using echocardiography) indicator 174 when the valve 110 is situated in a patient's heart. The operator can therefore determine the location and/or orientation of the valve and make adjustments accordingly.

Outer frame 170 is shown fully deformed, i.e., to the final, deployed configuration, in the side view and top view of FIGS. 6 and 7, respectively. As best seen in FIG. 7, the lower end of coupling portion 171 forms a roughly circular opening (identified by "O" in FIG. 7). The diameter of this opening preferably corresponds approximately to the fully deformed diameter of body portion 142 of inner frame 140 to facilitate the coupling together of these two components of valve 110.

Figure 8:
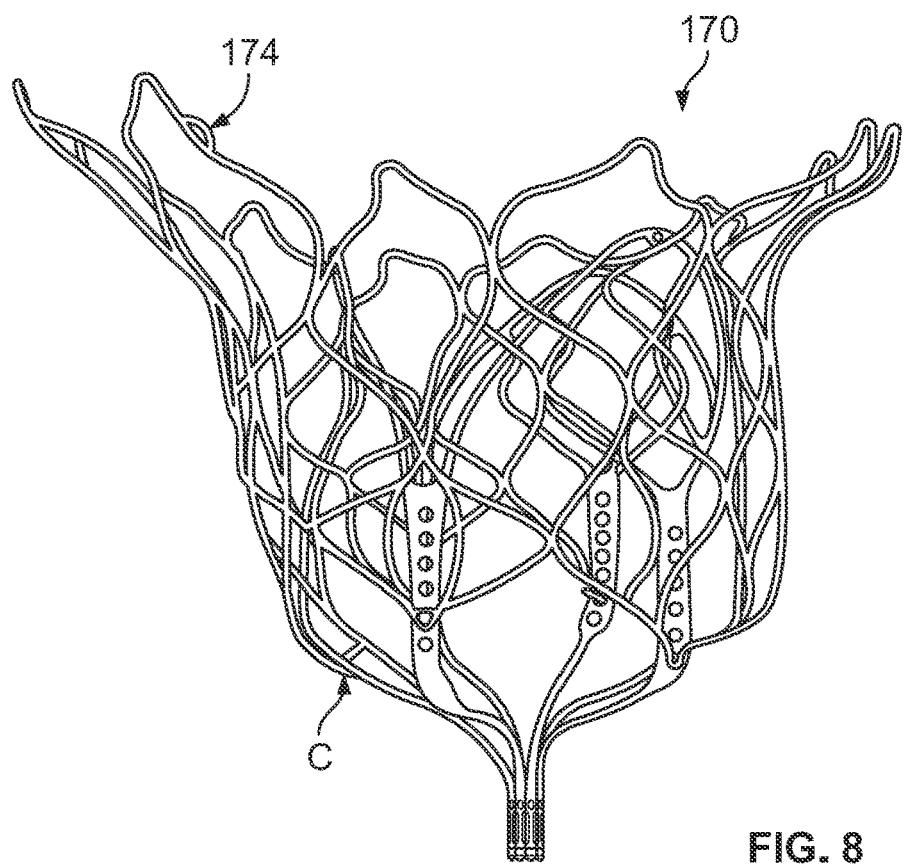
FIGS. 8-10 are side, front, and top views, respectively, of an assembly of the inner frame of FIGS. 2-4 and the outer frame of FIGS. 5-7, all in an expanded configuration.
Figure 9:
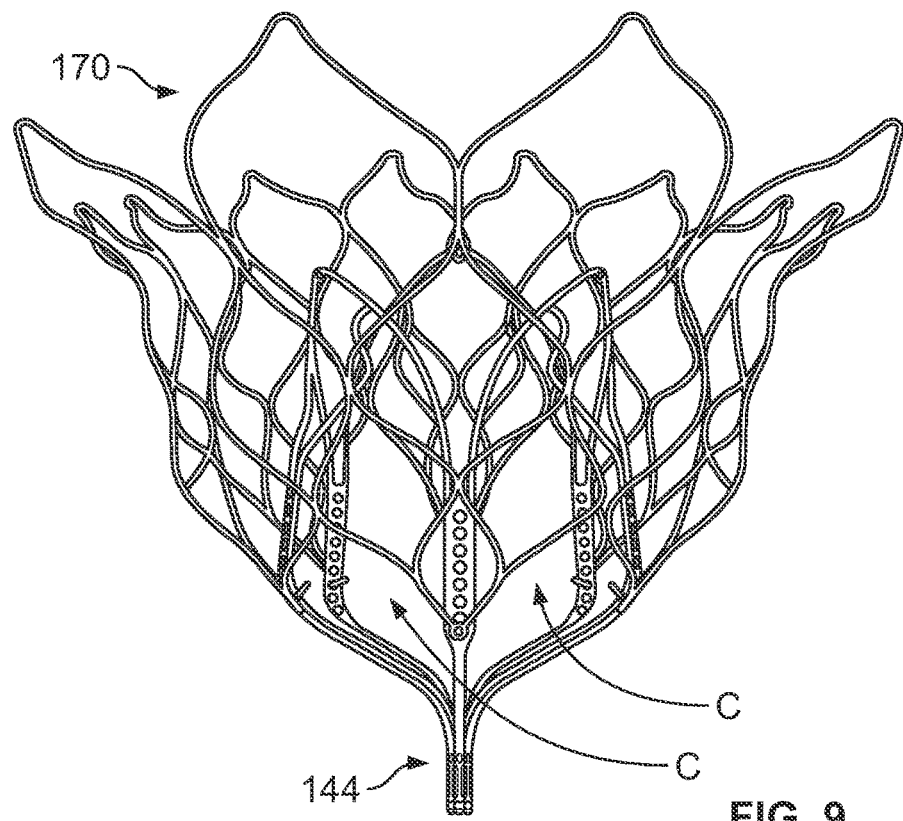
Figure 10:
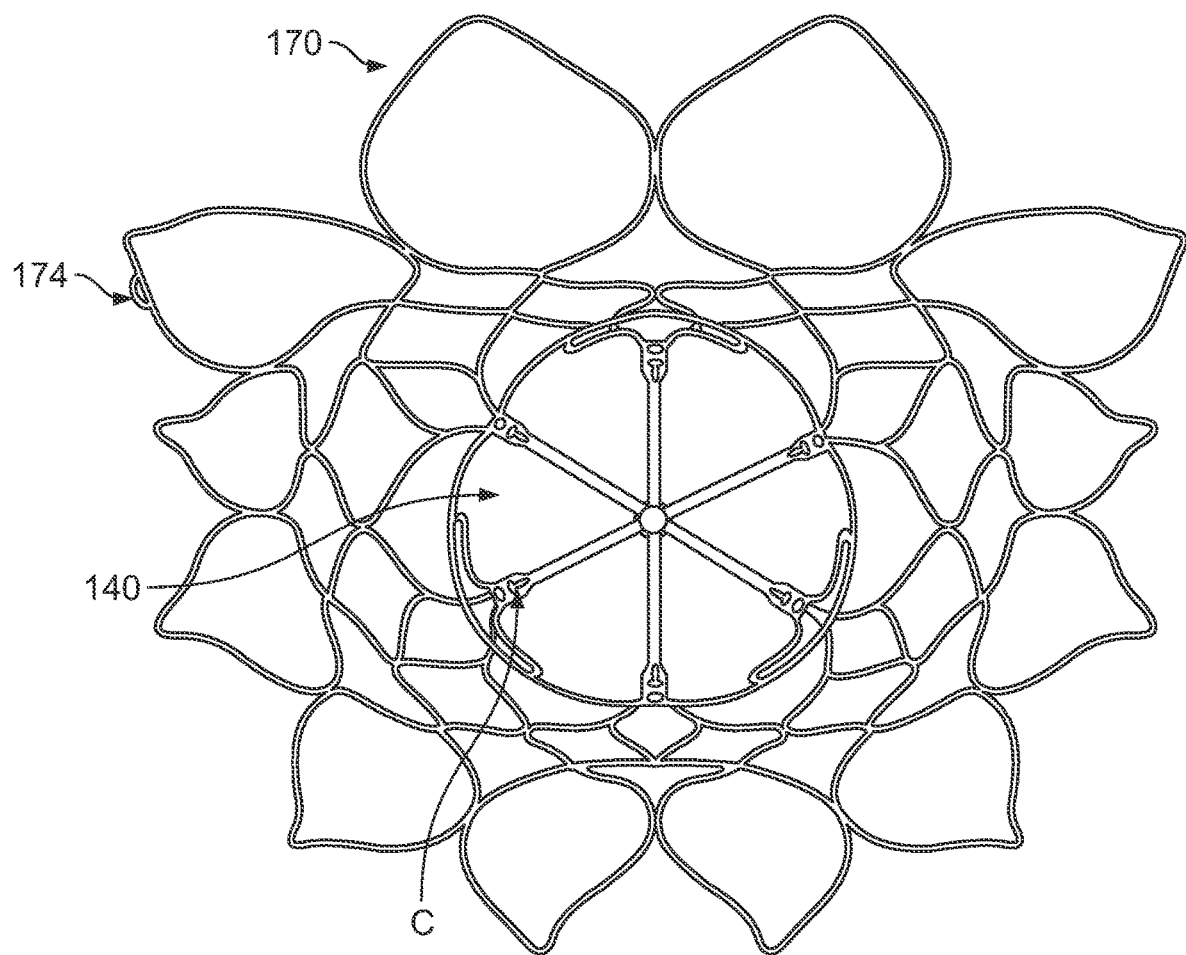

Outer frame 170 and inner frame 140 are shown coupled together in FIGS. 8-10 in front, side, and top views, respectively. The two frames collectively form a structural support for a valve leaflet structure, such as leaflet structure 136 in FIG. 1. The frames support leaflet structure 136 in the desired relationship to the native valve annulus, support the coverings for the two frames to provide a barrier to blood leakage between the atrium and ventricle, and couple to the tether 226 (by the inner frame 140) to aid in holding the prosthetic valve in place in the native valve annulus by the connection of the free end of the tether and tether anchor 210 to the ventricle wall, as described more fully below. The two frames are connected at six coupling points (representative points are identified as "C"). In this embodiment, the coupling of the frames is implemented with a mechanical fastener, such as a short length of wire, passed through an aperture 171A in coupling portion 171 of outer frame 170 and a corresponding aperture 142B in a longitudinal post 142A in body portion 142 of inner frame 140. Inner frame 140 is thus disposed within the outer frame 170 and securely coupled to it.

Figure 11A:
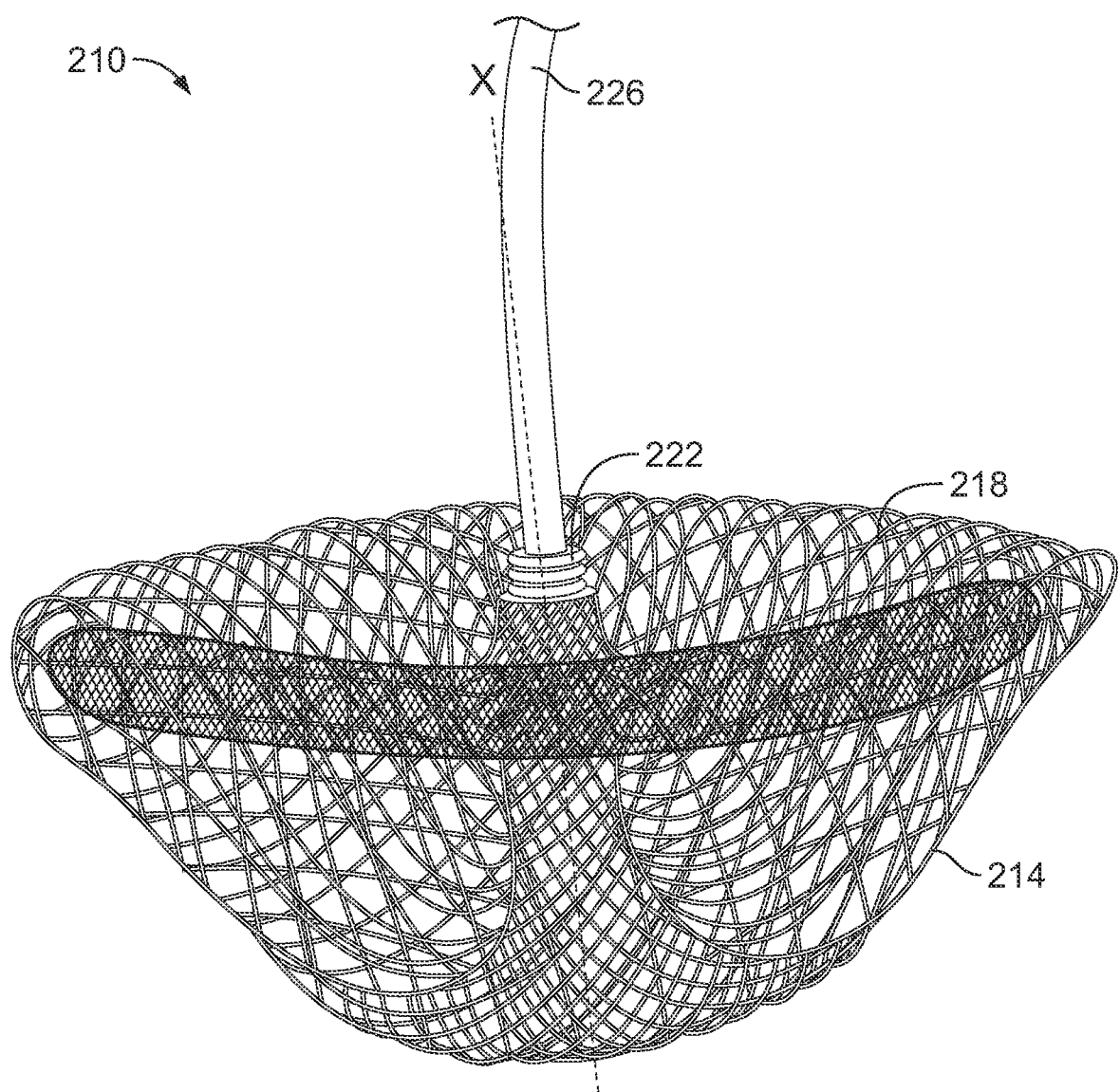
FIG. 11A is a perspective view of an anchor for the prosthetic valve of FIG. 1.
Figure 11B:
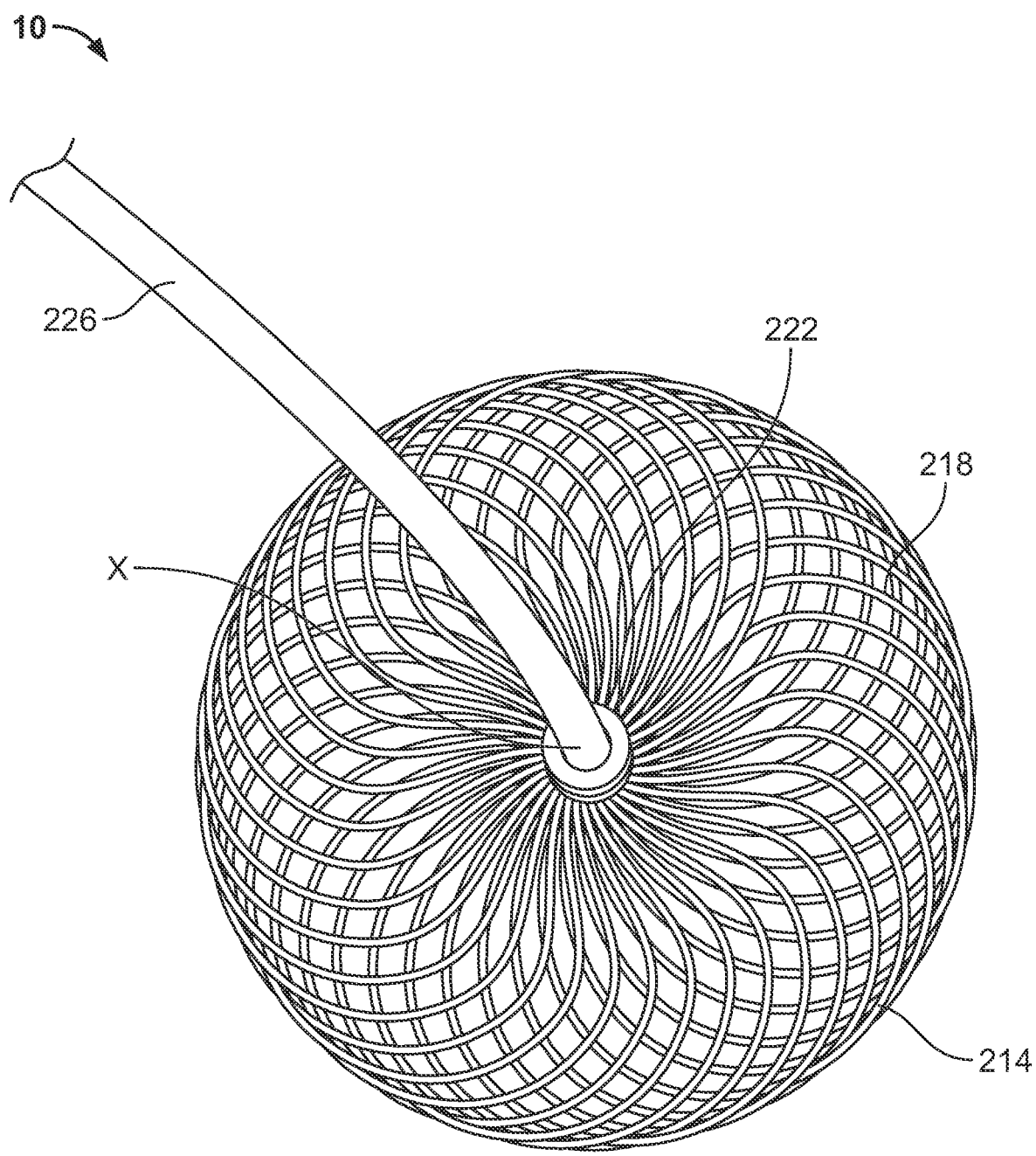
FIG. 11B is an axial view of the anchor of FIG. 11.

An exemplary anchor 210 for a prosthetic mitral heart valve is illustrated in FIGS. 11A and 11B. Anchor 210 includes a first disc 214 and a second disc 218, both provided by a wire mesh and centered on an axis X. First disc 214 is offset from second disc 218 in a first direction along axis X. First disc 214 and second disc 218 are each biased toward a dome-shaped resting configuration that is concave toward a second direction along axis X, the second direction being opposite the first direction. The resting configuration of first disc 214 extends far enough in the second direction along axis X to partially overlap second disc 218.

Figure 12:
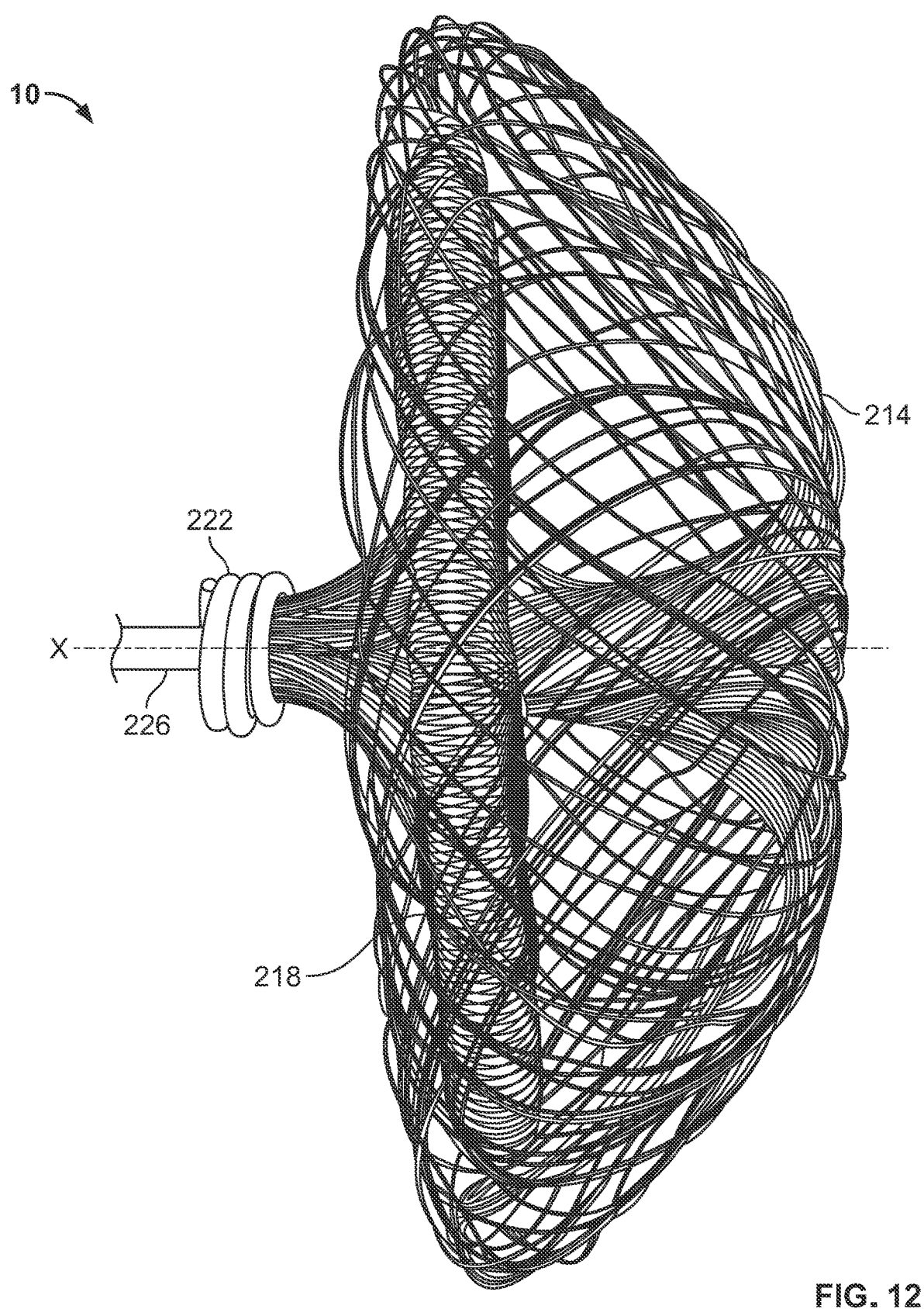
FIG. 12 is a side view of the anchor for the prosthetic valve of FIG. 1 according to another arrangement.

It should be understood that the illustrated dome shapes are merely exemplary, and first disc 214 and second disc 218 may be biased differently. For example, either or both of first disc 214 and second disc 218 may be biased toward a resting configuration that is convex toward the second direction or generally planar. Further, the first disc 214 and second disc 218 may be biased to different resting configurations. In one example, the first disc 214 may be biased toward a dome-shaped resting configuration that is concave toward the second direction while the second disc 218 is biased toward a generally planar configuration having about the same diameter location as the widest part of the dome-shaped resting configuration of the first disk 214, as shown in FIG. 12. In the arrangement shown in FIG. 12, second disc 218 is generally planar in shape with a shallow concavity toward the first direction near the center of second disc 218.

Anchor 210 also includes a cuff 222 for gripping a tether 226, which may be connected to a prosthetic heart valve. Cuff 222 is offset from second disc 218 in the second direction along axis X. One-way gripping features, such as angled teeth, within cuff 222 may permit anchor 210 to slide along tether 226 in the second direction, but not the first direction.

Figure 13:
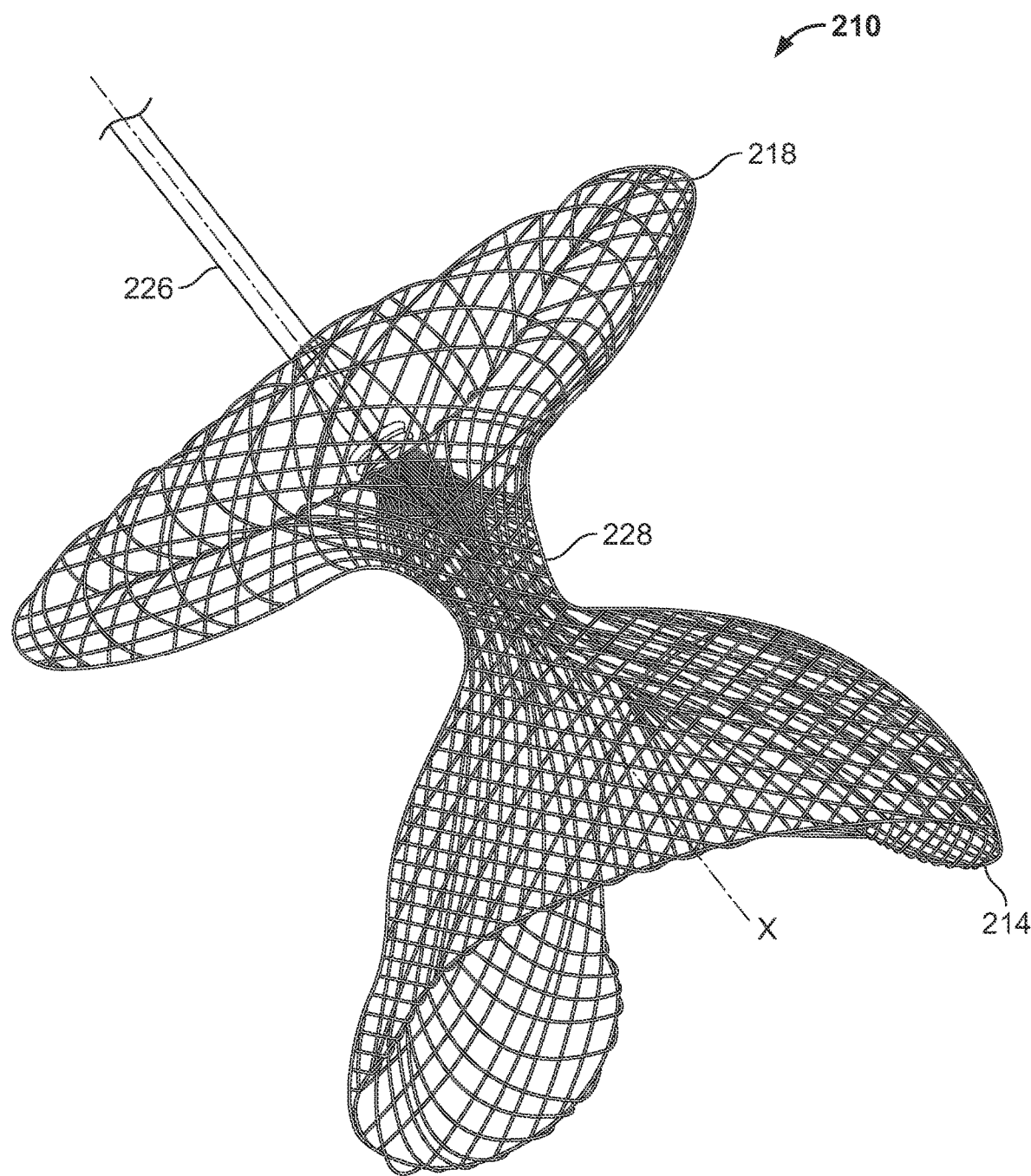
FIG. 13 is a perspective view of the anchor of FIG. 11 in a partially everted state.

Anchor 210 is flexible, as illustrated in FIG. 13, which shows anchor 210 with the first disc 214 everted from its resting configuration. First disc 214 is connected to second disc 218 by a neck 228 extending between first disc 214 and second disc 218. In the illustrated example, neck 228 is centered on axis X, but in other examples neck 228 may be radially offset from axis X. First disc 214, second disc 218, and neck 228 may all be constructed from a single continuous piece or tube of wire mesh. The wire mesh may be formed from a plurality of strands or wires braided into various three-dimensional shapes and/or geometries to engage tissues, or from one or more sheets cut to provide mesh, such as by laser. In one example, the wires form a braided metal fabric that is resilient, collapsible and capable of heat treatment to substantially set a desired shape. One class of materials which meets these qualifications is shape-memory alloys, such as nitinol. The wires may comprise various materials other than nitinol that have elastic and/or memory properties, such as spring stainless steel, trade named alloys such as Elgiloy® and Hastelloy®, CoCrNi alloys (e.g., tradename Phynox®), MP35N®, CoCrMo alloys, or a mixture of metal and polymer fibers. Depending on the individual material selected, the strand diameter, number of strands, and pitch may be altered to achieve the desired shape and properties of anchor 210. Shape memory materials such as nitinol may be particularly suitable for anchor 210 in that shape memory material construction enables anchor 210 to consistently return to an intended shape after being compressed and deployed. In other arrangements, anchor 210 may be covered by or may incorporate other flexible biocompatible material, such as a fabric.

Figure 14:
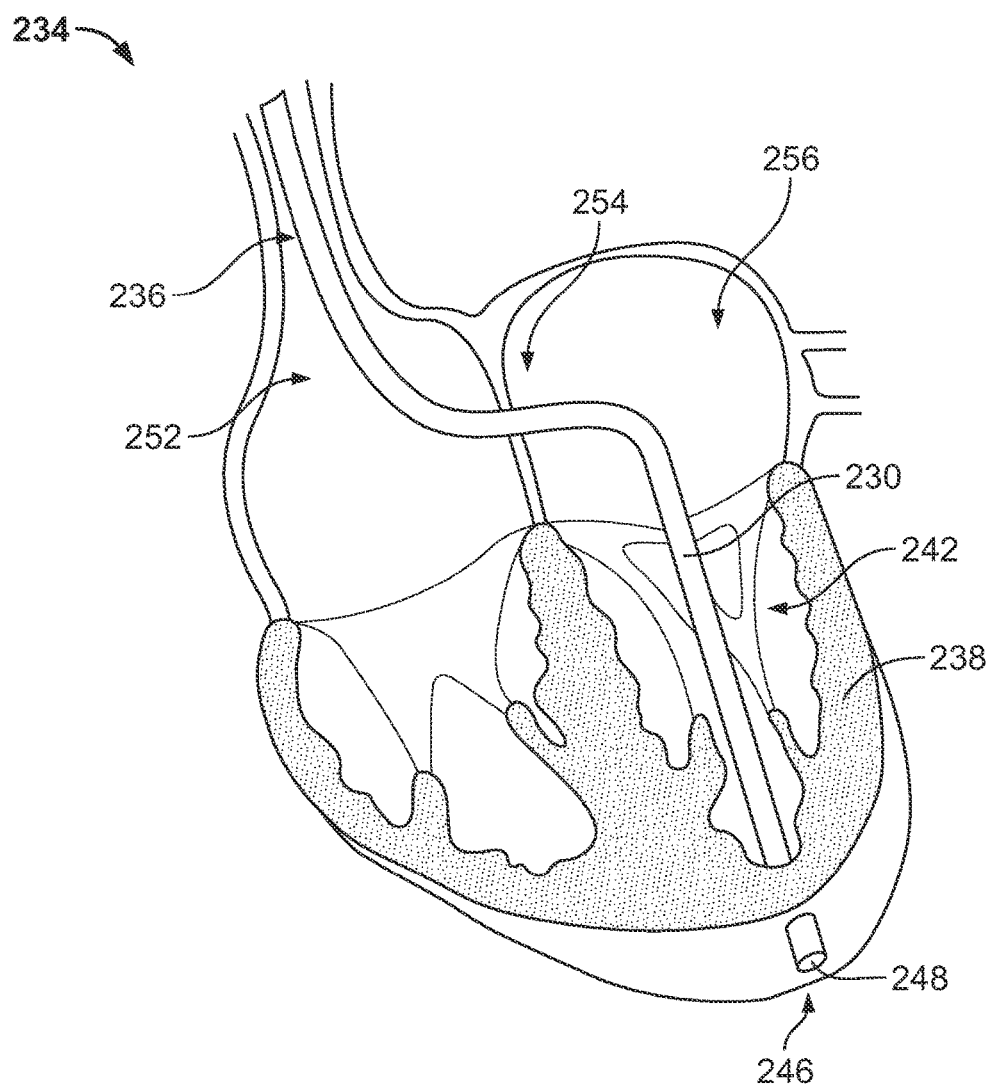
FIG. 14 illustrates a trans-jugular insertion of a delivery tube for the anchor of FIG. 11.

FIG. 14 shows a trans-jugular insertion of an at least partially flexible delivery tube 230 for anchor 210 and valve 110. Delivery tube 230 may be formed of any known material for building catheters, including biocompatible metals such as steel, and may be part of a steerable or flexible catheter system. Delivery tube 230 may include an inflexible portion near its distal end to facilitate the intended puncture of tissue and guidance of valve 110. Delivery tube 230 is inserted through the patient's jugular vein (not shown), then through superior vena cava 236, right atrium 252, atrial septum 254, left atrium 256, native mitral valve 260, and into left ventricle 242. Tube 230 exits left ventricle 242 through ventricular wall 238 at or near the apex 246 of heart 234. A retractable puncturing device (not shown) and a retractable atraumatic tip (not shown) may extend from the distal open end 248 of tube 230 in alternate stages of insertion of tube 230. The puncturing device may produce openings through atrial septum 254 and ventricular wall 238 while the atraumatic tip may act to prevent injury to other tissue. Once delivery tube 230 has been fully inserted, the distal open end 248 of tube 230 is positioned outside of ventricular wall 238. The trans-jugular insertion of tube 230 may be accomplished by any of variety of methods, such as, for example, guiding tube 230 along a guide wire, such as a shape-memory guide wire, inserted through the jugular vein. The flexible nature of anchor 210 allows trans-jugular delivery of anchor 210 through tube 230. Because tube 230, anchor 210, and valve 110 all reach heart 234 from the jugular vein, valve 110 and anchor 210 may be delivered and implanted without any intercostal puncture.

Figure 15:
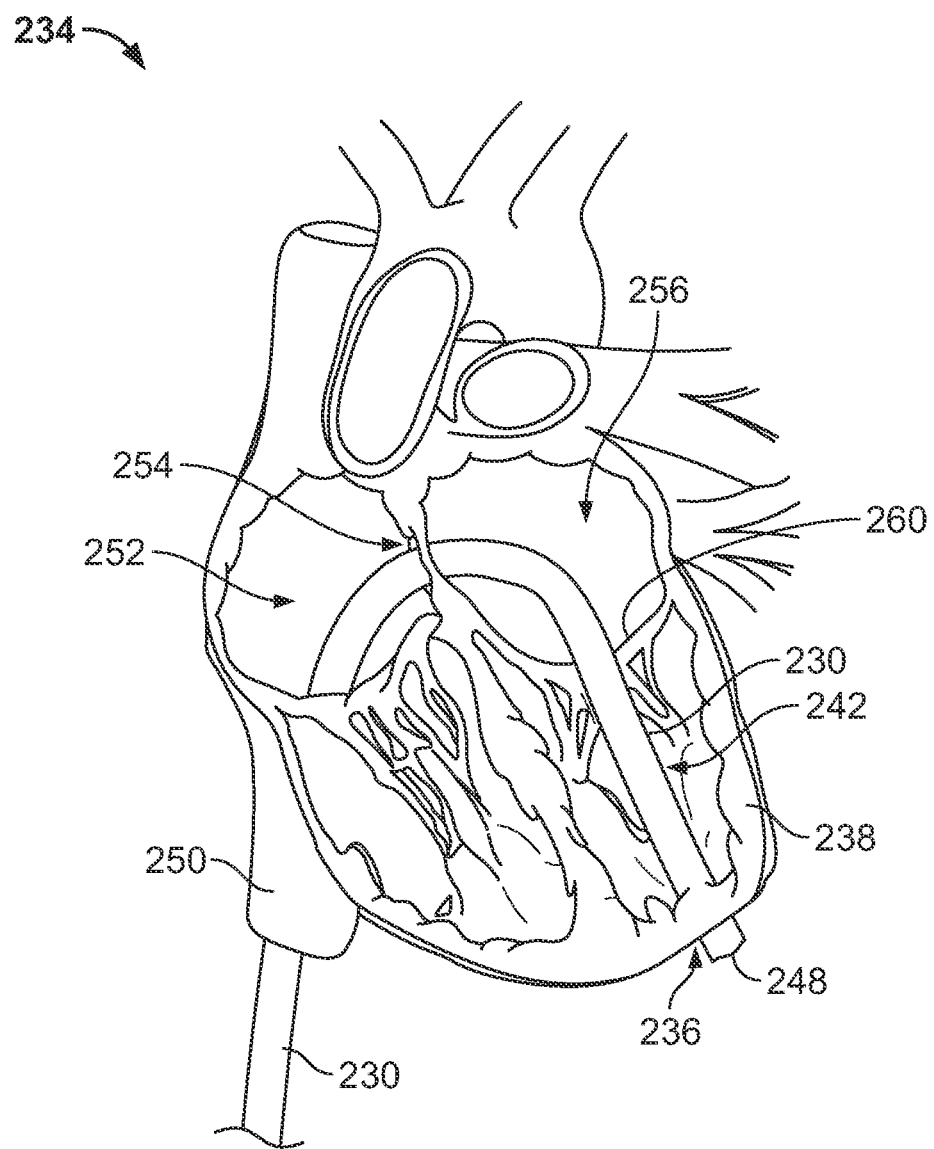
FIG. 15 illustrates a trans-femoral insertion of the delivery tube of FIG. 14.
Figure 16:
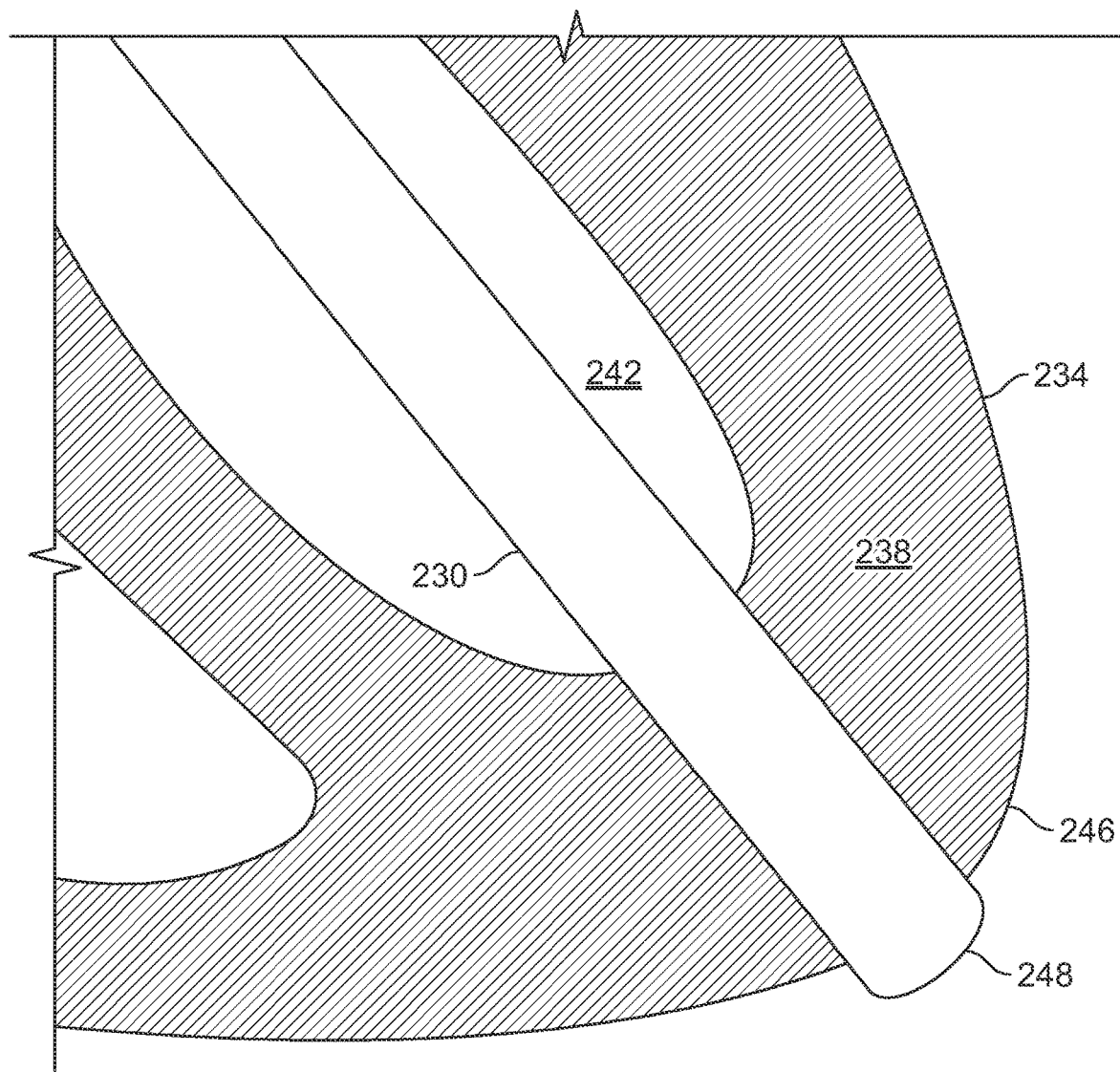
FIG. 16 illustrates the delivery tube of FIGS. 14 and 15 extending through a wall of a heart.

FIG. 15 shows a trans-femoral insertion of tube 230. Tube 230 enters heart 234 through inferior vena cava 250, travels through right atrium 252, and punctures septum 254 to enter left atrium 256. Tube 230 is advanced from left atrium 256 through native mitral valve 260, left ventricle 242, and ventricular wall 238 such that the open end 248 of the tube is positioned outside of wall 238 at or near apex 246. As with trans-jugular insertion, guidance of tube 230 during trans-femoral insertion may be accomplished using a variety of methods, including guidance along a guide wire.

The trans-jugular and trans-femoral insertions described above are merely exemplary. It should be understood that tube 230 could be guided toward heart 234 using any suitable method known in the art.

Figure 17:
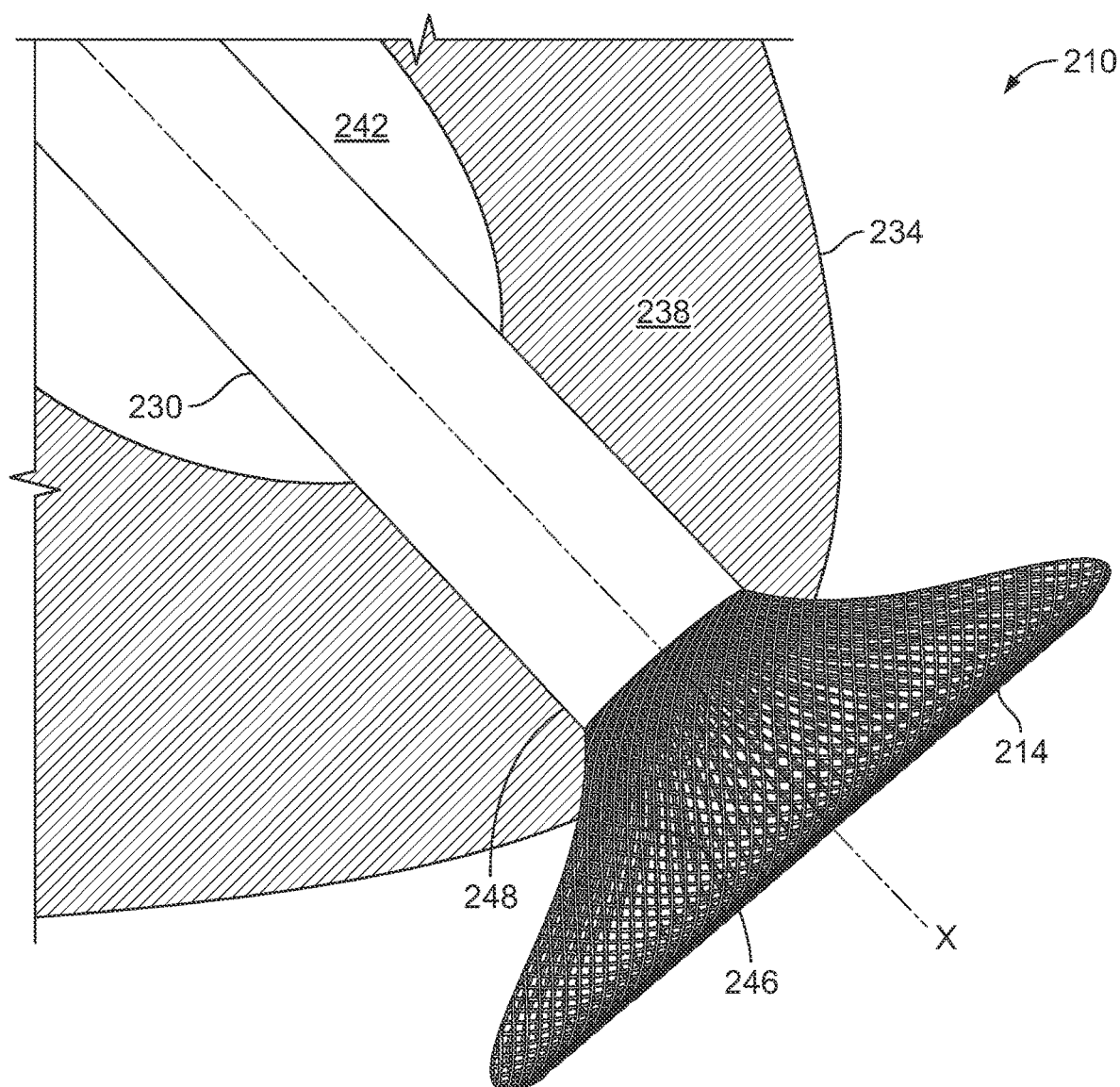
FIGS. 17-20 illustrate the anchor of FIG. 11 in progressive stages of deployment from the delivery tube of FIGS. 14 and 15.
Figure 18:
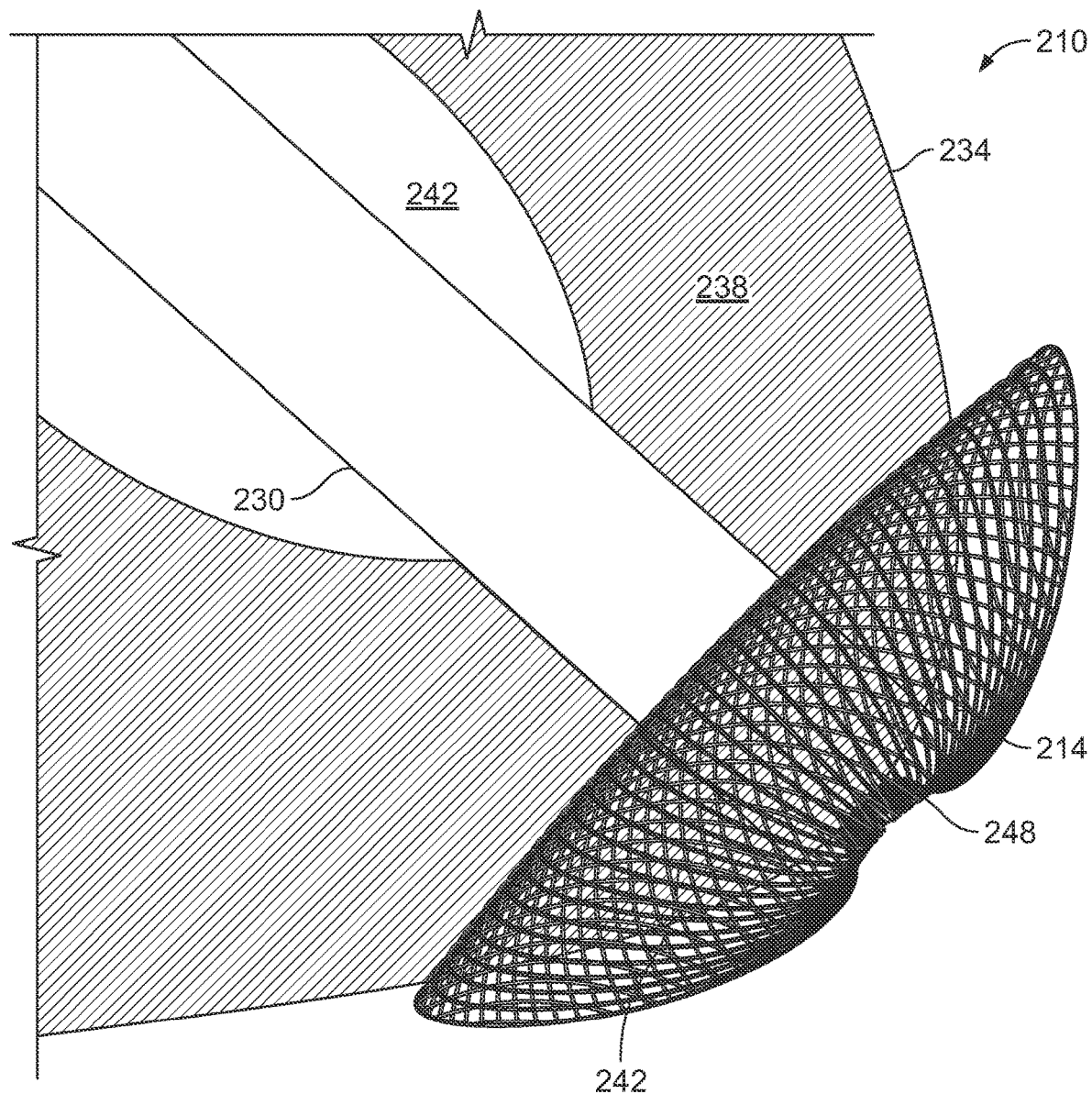
Figure 19:
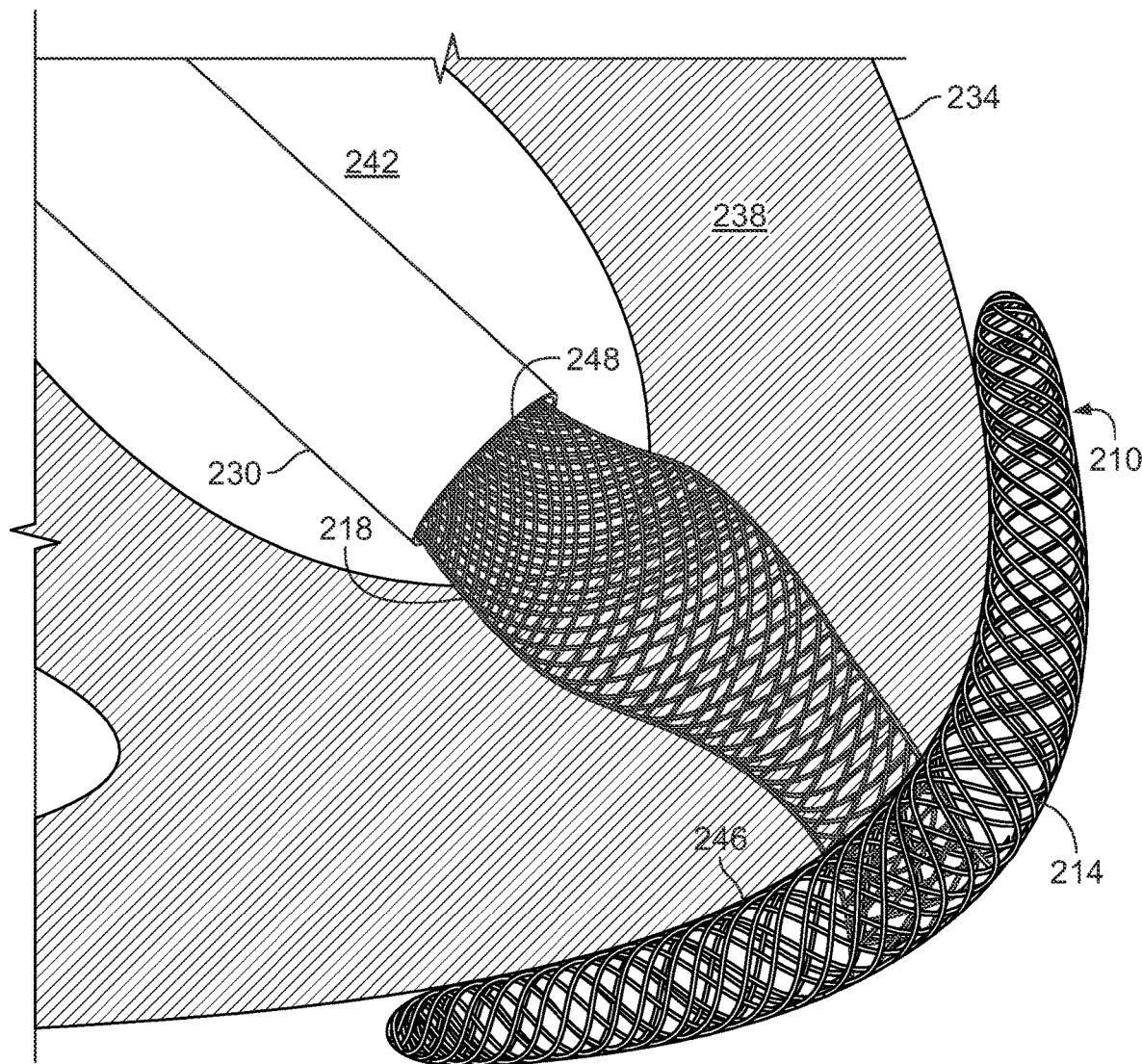
Figure 20:
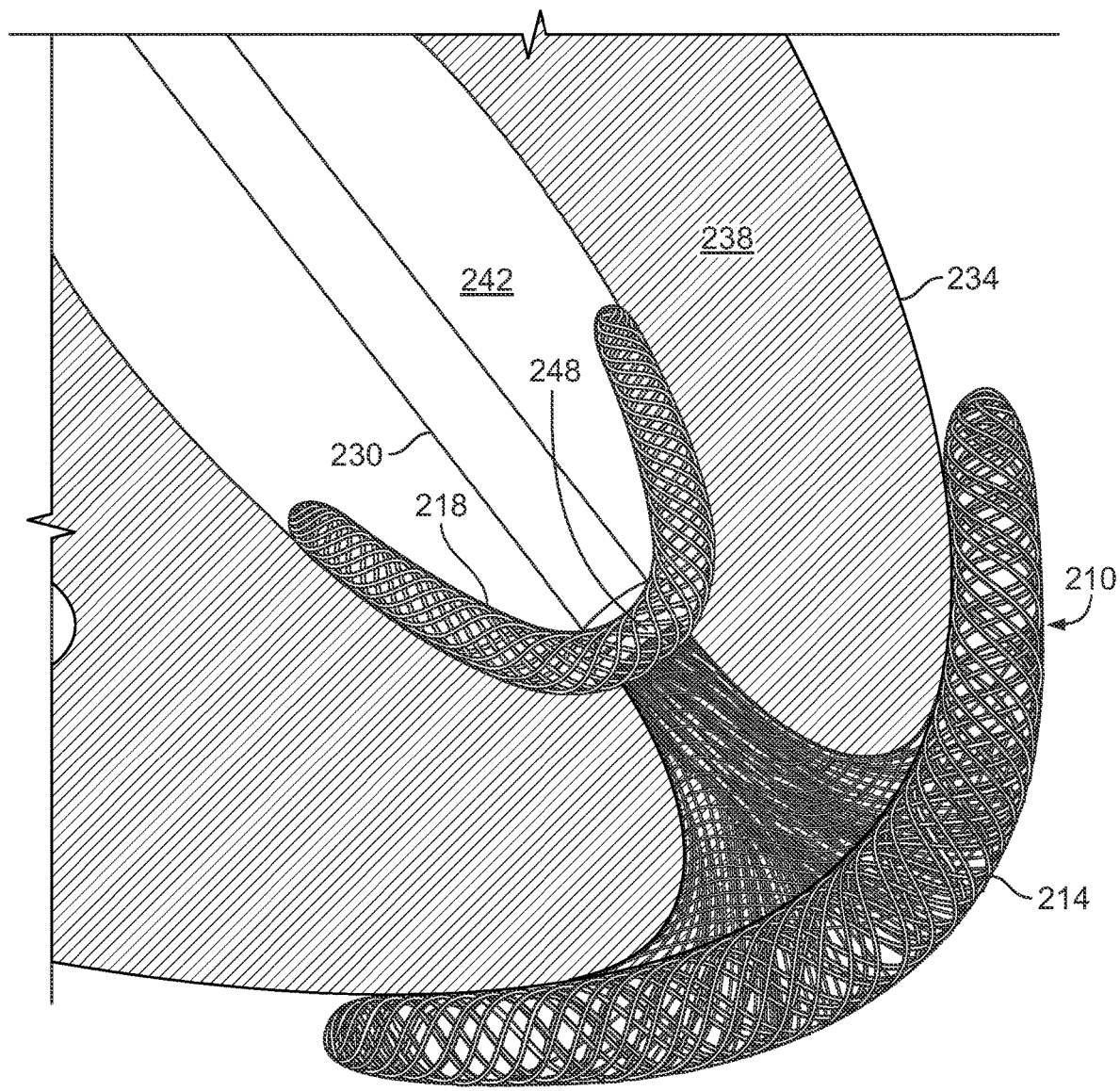
Figure 21A:
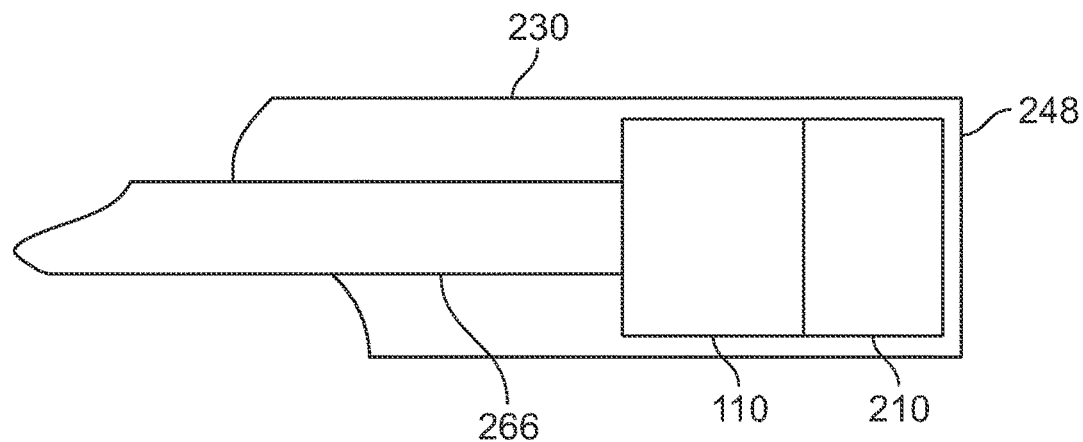
FIGS. 21A and 21B illustrate the delivery tube being retracted from the prosthetic valve of FIG. 1 and the anchor of FIG. 11.
Figure 21B:
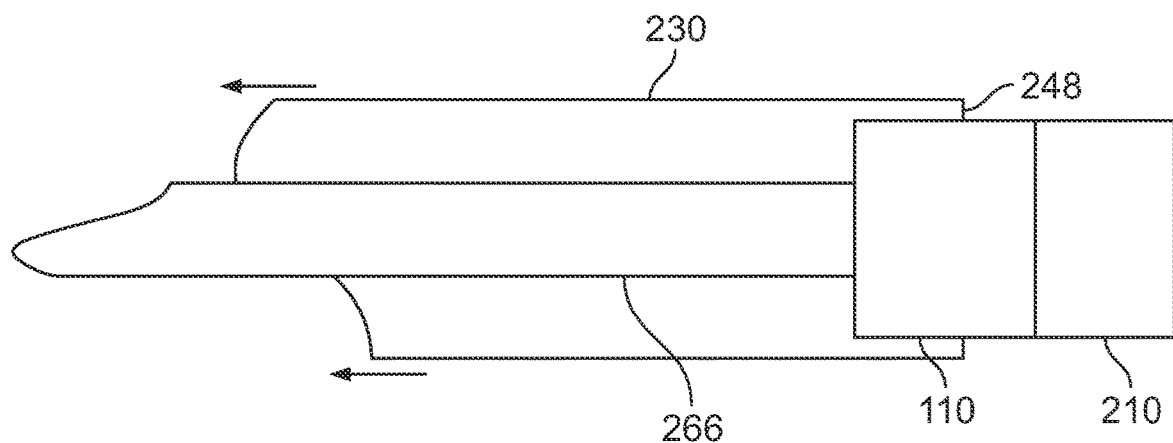

FIGS. 16-20 illustrate anchor 210 in progressive stages of deployment from the open end 248 of tube 230. Tube 230 is shown in a distalmost position in FIG. 16, with open end 248 positioned outside of heart 238. Tube 230 may be retracted while anchor 210 is forced to remain in place, such as by a reversal of a typical Bowden cable arrangement. For example, a semi-rigid cable or wire 266 may be inserted through tube 230 to contact the proximal end of valve 110, as shown in FIG. 21A. Pulling tube 230 proximally relative to wire 266 causes valve 110 and anchor 210 to deploy out from the open end 248 of tube 230, as shown in 21B. As shown in FIG. 17, retracting tube 230 while preventing anchor 210 from retreating with the tube into heart 234 causes first disc 214 of anchor 210 to deploy out from the open end 248 of tube 230 and expand radially relative to axis X. Upon further retraction of tube 230, the bias of first disc 214 causes it to curve back onto the outer apex 246 of heart 234, as shown in FIG. 18. Further retraction of tube 230 in FIG. 19 allows second disc 218 to deploy and expand radially relative to axis X within left ventricle 242 until second disc 218 opens to press against an inner side of wall 238, as shown in FIG. 20. Pressure against wall 238 results from the elastic bias of first disc 214 and second disc 218 toward certain resting positions as described above with regard to FIGS. 11A, 11B, and 12. First disc 214 and second disc 218 pressing on opposite sides of wall 238 causes anchor 210 to grip wall 238. Such progressive expansion from within a narrow tube results in anchor 210 adequately securing valve 110 to ventricular wall 238 without requiring an intercostal puncture through the patient's chest.

According to alternative embodiments or arrangements, tube 230 may be retracted while anchor 210 is held in place by a cord (not shown) connected to anchor 210 and extending out from an intercostal incision in the patient's chest. In an embodiment employing this method, tube 230 may extend into left ventricle 242 but not entirely or at all through ventricular wall 238, and anchor 210 may be deployed by pulling anchor 210 out of tube 230 and through wall 238 using the cord.

Figure 22:
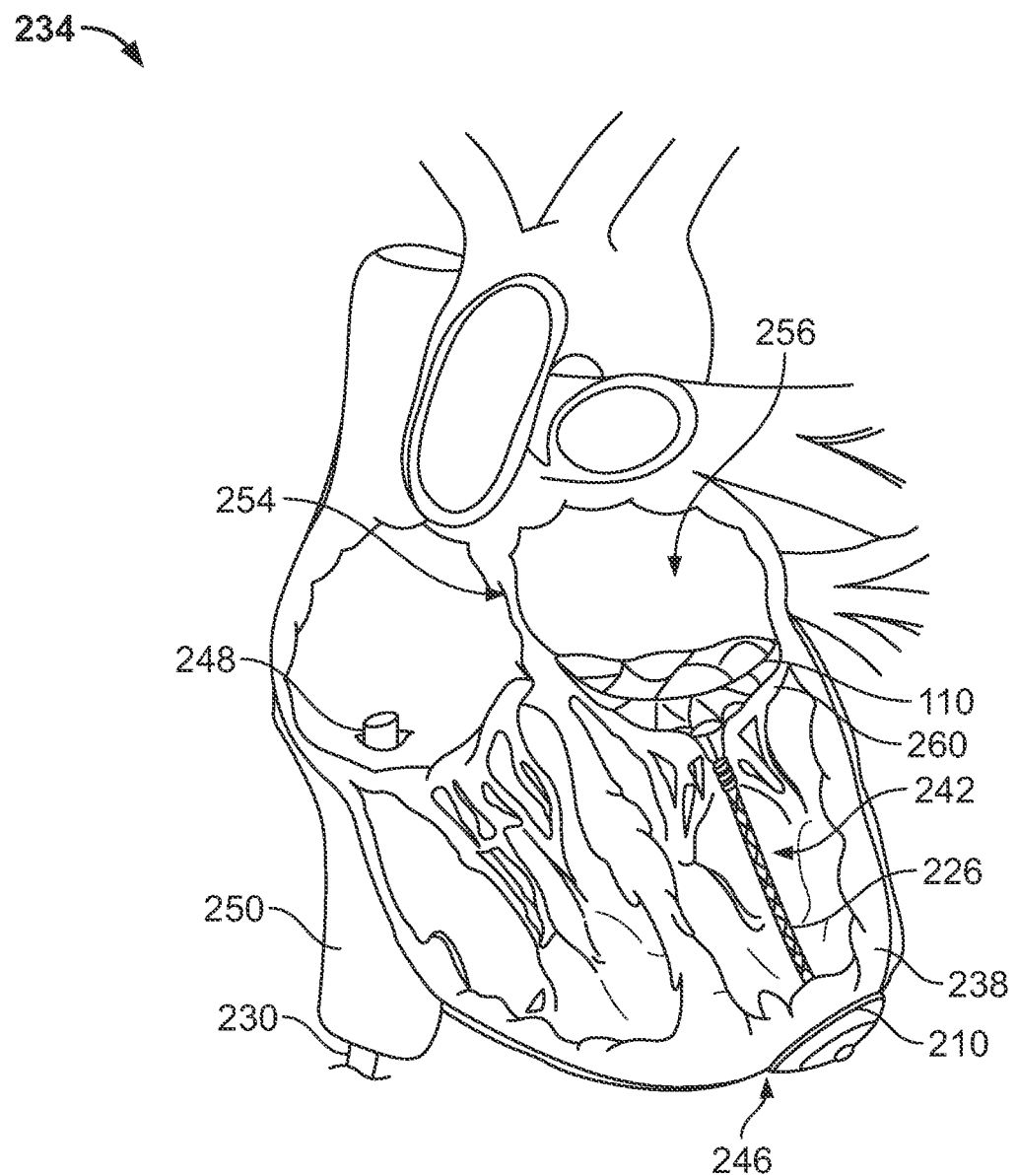
FIG. 22 illustrates the valve of FIG. 1 implanted in a heart.

FIG. 22 illustrates valve 110 implanted in heart 234 with anchor 210 seated at or near the apex 246 of heart 234. Tube 230 has been withdrawn from heart 234, through inferior vena cava 250 in the illustrated example, leaving valve 110 behind.

Figure 23B:
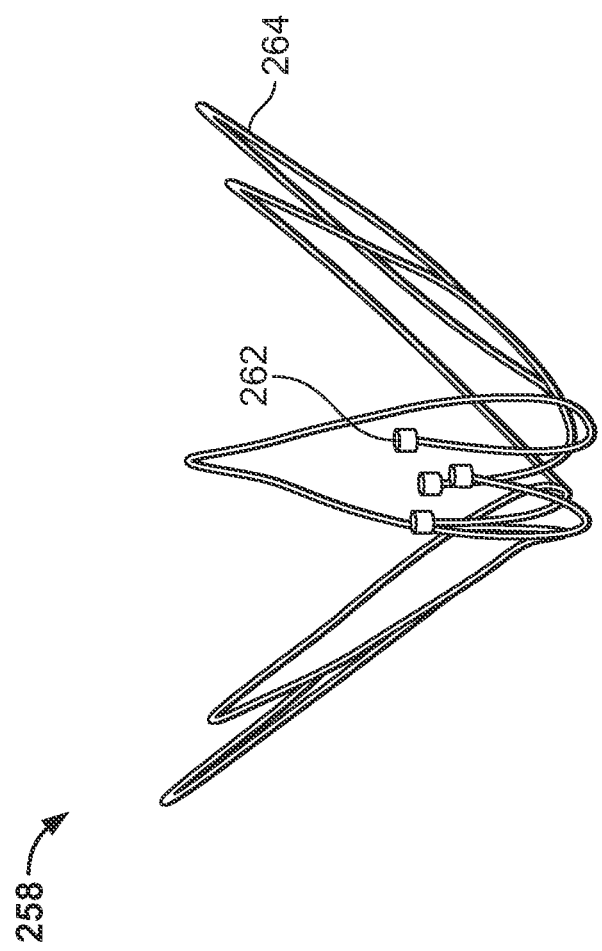
FIGS. 23A and 23B are perspective views of a frame for the anchor of FIG. 11.
Figure 23A:
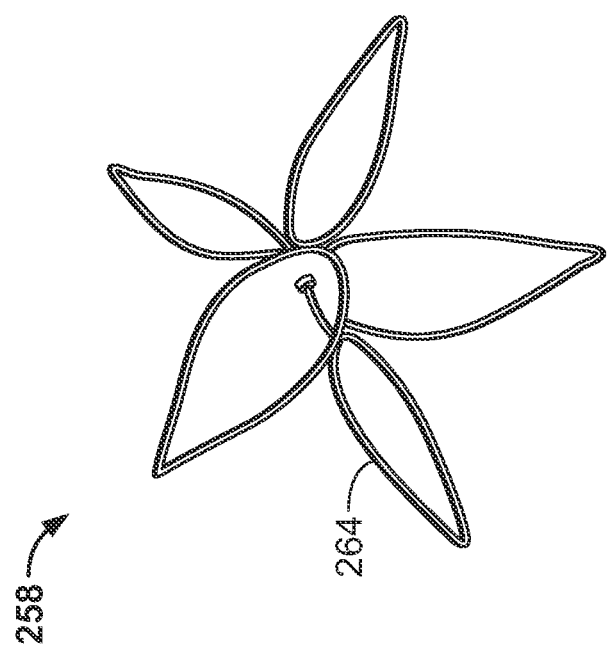

FIGS. 23A and 23B illustrate a flexible reinforcing frame 258 for anchor 210. Frame 258 optionally may be installed as illustrated to reinforce anchor 210. Frame 258 is constructed from wire that is both thicker and less flexible than the wire mesh of anchor 210 (or simply less flexible), but frame 258 may be constructed from any suitable elastically deformable biocompatible material, such as nitinol. Frame 258 tends toward a resting configuration in which leaves 264 of frame 258 are arranged to form a cone shape. Frame 258 may be inverted from the cone shape, but will return to the cone shape upon release from external forces.

Figure 24:
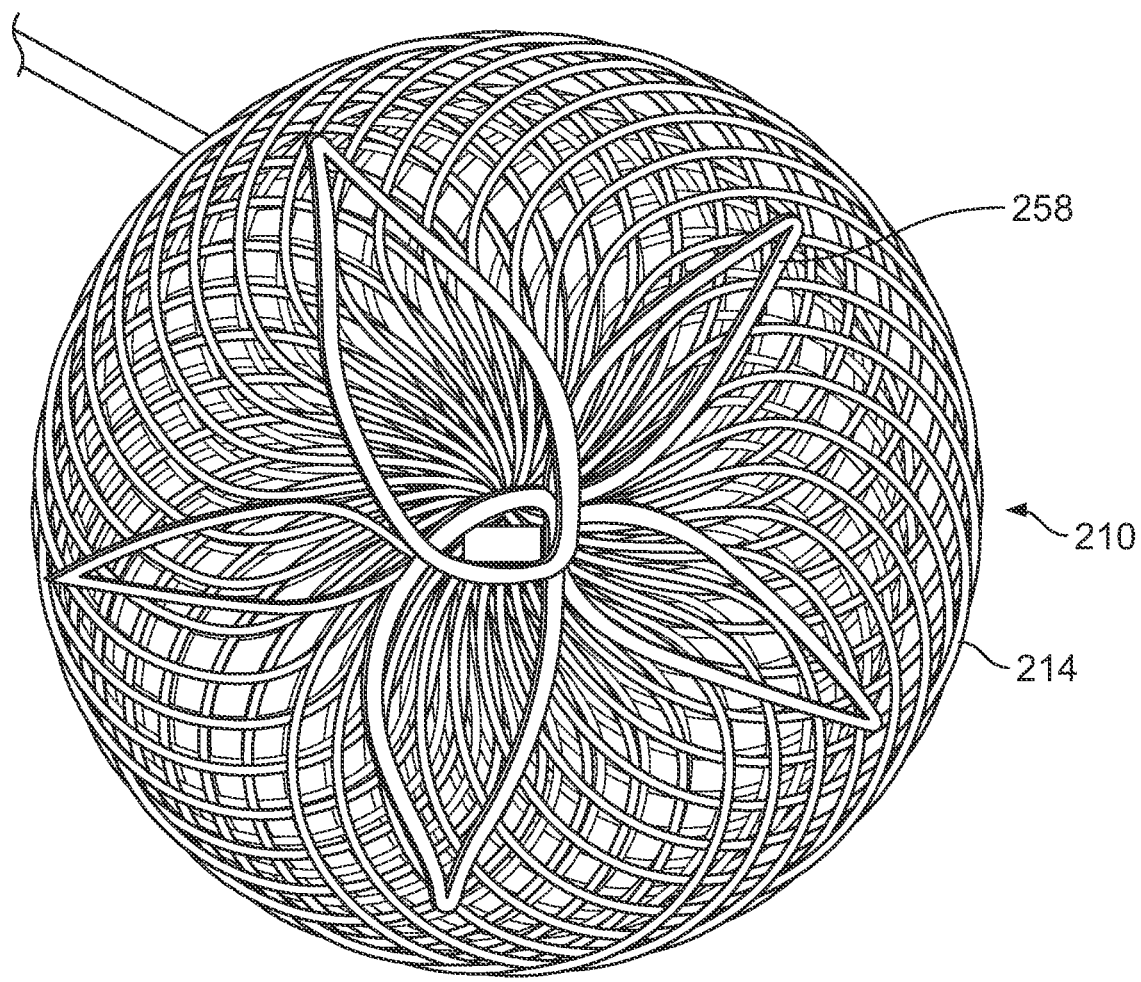
FIG. 24 is an axial view of the anchor of FIG. 11 with the frame of FIGS. 23A and 23B installed.

FIG. 24 shows frame 258 installed on anchor 210. Frame 258 is disposed over first disc 214, on a side of first disc 214 opposite second disc 218. Tabs 262 extend from frame 258 axially through the neck 228 of anchor 210 and are bound to tether 226 by cuff 222. In such an arrangement, frame 258 would be inverted and compressed radially inward so as to extend in the first direction relative to anchor 210 when anchor 210 is compressed within tube 230. For example, first disc 214 and frame 258 may be inverted to extend in the first direction along axis X within tube 230 prior to delivery. Frame 258 will fold back toward the second direction and into the cone shape after release from tube 230. Frame 258 further includes tabs 262 that, in the rest configuration of frame 258, extend into an interior of the cone shape from a point at which leaves 264 intersect. As anchor 210 is deployed, frame 258 expands radially outward and folds backward toward the second direction and ventricular wall 238 to push first disc 214 onto wall 238. Tabs 262 may extend into cuff 222, and frame 258 may be connected to anchor 210 by cuff 222 gripping tabs 262.

To summarize the foregoing, disclosed is an anchor for a prosthetic heart valve, including a flexible first disc biased toward a first shape that is convex in a first direction; a neck extending from the first disc in a second direction opposite the first direction, the neck having a first end connected to the first disc and a second end; and a flexible second disc connected to the second end of the neck and biased toward a second shape; and/or the first disc, the neck, and the second disc may be formed from a flexible tube; and/or the tube may be formed of braided wire; and/or the first disc and the second disc may be formed of wire mesh; and/or the wire mesh may be constructed of a shape memory alloy; and/or the anchor may further include an annular cuff connected to the second disc and configured to secure the anchor to a tether; and/or the cuff may include gripping features that restrict movement of the tether within the cuff in the second direction and permit movement of the tether within the cuff in the first direction; and/or the first shape may be a first dome shape and the second shape may be a second dome shape that is convex in the first direction; and/or the first dome shape may have a concave interior, and the second dome shape may extend into the concave interior; and/or the anchor may further include a deformable frame supporting the first disc; and/or the frame may be invertible and may be biased toward a cone shape.

Also disclosed is a prosthetic heart valve, including a valve portion including at least two leaflets; a tether having a first end connected to the valve portion and a second end; and a flexible anchor connected to the second end of the tether, the anchor including a flexible first disc biased toward a first shape that is convex in a first direction; a flexible second disc connected to the first disc and biased toward a second shape; and a cuff securing the second disc to the tether; and/or the cuff may include gripping features that restrict movement of the tether within the cuff in the second direction and permit movement of the tether within the cuff in the first direction. Also disclosed is a method of anchoring any of the prosthetic heart valves described above to the heart of a patient, the method including disposing the anchor within a delivery tube near a distal end of the delivery tube; passing the distal end of the delivery tube at least partially through a wall of the heart; and deploying the anchor from the delivery tube such that the first disc is positioned outside the heart wall and the second disc is positioned inside the heart wall; and/or the method may further include inserting the delivery tube into the patient through a femoral vein; and/or the method may further include passing the delivery tube through a septum of the heart; and/or the step of deploying the anchor may include restraining movement of the anchor relative to the heart; and/or the step of deploying the anchor may include pushing the anchor out of the distal end of the tube.

Also disclosed is a prosthetic heart valve, including a valve portion including at least two leaflets; a tether having a first end connected to the valve portion and a second end; and a flexible anchor connected to the second end of the tether, the anchor including a flexible first disc biased toward a first shape that is convex in a first direction; a neck having a first end connected to the first disc and extending in a second direction opposite the first direction to a second end; a flexible second disc connected to the second end of the neck, the second disc being biased toward a second shape that is convex in the first direction, the first disc, the neck, and the second disc being formed from a contiguous tube of wire mesh; a deformable frame supporting the first disc, the frame being invertible and biased toward a cone shape; and an annular cuff securing the second disc to the tether.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
a valve portion including at least two leaflets;
a tether having a first end connected to the valve portion and a second end; and
a flexible anchor connected to the second end of the tether, the anchor comprising:
a flexible first disc biased toward a first shape that is convex in a first direction;
a flexible second disc connected to the first disc and biased toward a second shape;
a neck extending from the first disc in a second direction opposite the first direction, the neck having a first end connected to the first disc and a second end; and
a cuff securing the second disc to the tether;
wherein the cuff includes one-way gripping features that permit the anchor to slide along the tether in the second direction, but do not allow the anchor to slide along the tether in the first direction.

2. The prosthetic heart valve of claim 1, wherein the first disc, the neck, and the second disc are formed from a flexible tube.

3. The prosthetic heart valve of claim 2, wherein the tube is formed of braided wire.

4. The prosthetic heart valve of claim 1, wherein the first disc and the second disc are formed of wire mesh.

5. The prosthetic heart valve of claim 4, wherein the wire mesh is constructed of a shape memory alloy.

6. The prosthetic heart valve of claim 1, wherein the first shape is a first dome shape and the second shape is a second dome shape that is convex in the first direction.

7. The prosthetic heart valve of claim 6, wherein the first dome shape has a concave interior, and the second dome shape extends into the concave interior.

8. The prosthetic heart valve of claim 1, further comprising a deformable frame supporting the first disc.

9. The prosthetic heart valve of claim 8, wherein the frame is invertible and is biased toward a shape that is convex in the first direction.

10. A method of anchoring the prosthetic heart valve of claim 1 to the heart of a patient, the method comprising:
disposing the anchor within a delivery tube near a distal end of the delivery tube;
locating the distal end of the delivery tube near or through a wall of the heart; and
deploying the anchor from the delivery tube such that the first disc is positioned outside the heart wall and the second disc is positioned inside the heart wall.

11. The method of claim 10, further comprising inserting the delivery tube into the patient through a femoral vein.

12. The method of claim 10, further comprising passing the delivery tube through a septum of the heart.

13. The method of claim 10, wherein the step of deploying the anchor includes restraining movement of the anchor relative to the heart.

14. The method of claim 10, wherein the step of deploying the anchor includes pushing the anchor out of the distal end of the tube.

15. A prosthetic heart valve, comprising:
a valve portion including at least two leaflets;
a tether having a first end connected to the valve portion and a second end; and
a flexible anchor connected to the second end of the tether, the anchor comprising:
a flexible first disc biased toward a first shape that is convex in a first direction;
a neck having a first end connected to the first disc and extending in a second direction opposite the first direction to a second end;
a flexible second disc connected to the second end of the neck, the second disc being biased toward a second shape that is convex in the first direction, the first disc, the neck, and the second disc being formed from a contiguous tube of wire mesh;
a deformable frame supporting the first disc, the frame being invertible and biased toward a cone shape; and
an annular cuff securing the second disc to the tether.

* * * * *